US009717781B2

(12) United States Patent
Shneider et al.

(10) Patent No.: US 9,717,781 B2
(45) Date of Patent: Aug. 1, 2017

(54) METHODS AND COMPOSITIONS RELATING TO P62 FOR THE TREATMENT AND PROPHYLAXIS OF CANCER

(76) Inventors: Alexander Shneider, Needham, MA (US); Franco Venanzi, Camerino (IT); Michael Sherman, Newton, MA (US); Victor Shifrin, Newton, MA (US)

( * ) Notice: Subject to any disclaimer, the term of this patent is extended or adjusted under 35 U.S.C. 154(b) by 0 days.

(21) Appl. No.: 14/236,829

(22) PCT Filed: Aug. 8, 2012

(86) PCT No.: PCT/US2012/050024
§ 371 (c)(1),
(2), (4) Date: Feb. 3, 2014

(87) PCT Pub. No.: WO2013/022991
PCT Pub. Date: Feb. 14, 2013

(65) Prior Publication Data
US 2014/0161824 A1    Jun. 12, 2014

Related U.S. Application Data

(60) Provisional application No. 61/521,280, filed on Aug. 8, 2011.

(51) Int. Cl.
| | |
|---|---|
| *A61K 31/713* | (2006.01) |
| *A61K 47/42* | (2017.01) |
| *A61K 39/00* | (2006.01) |
| *A61K 45/06* | (2006.01) |
| *A61K 31/337* | (2006.01) |
| *A61K 31/407* | (2006.01) |
| *A61K 31/475* | (2006.01) |
| *A61K 31/675* | (2006.01) |
| *A61K 31/704* | (2006.01) |
| *A61K 31/7068* | (2006.01) |
| *A61K 38/17* | (2006.01) |
| *A61K 38/19* | (2006.01) |
| *A61N 5/10* | (2006.01) |
| *A61K 9/00* | (2006.01) |
| *A61K 48/00* | (2006.01) |

(52) U.S. Cl.
CPC ........ *A61K 39/0011* (2013.01); *A61K 31/337* (2013.01); *A61K 31/407* (2013.01); *A61K 31/475* (2013.01); *A61K 31/675* (2013.01); *A61K 31/704* (2013.01); *A61K 31/7068* (2013.01); *A61K 38/1709* (2013.01); *A61K 38/1793* (2013.01); *A61K 38/19* (2013.01); *A61K 45/06* (2013.01); *A61N 5/10* (2013.01); *A61K 9/0019* (2013.01); *A61K 48/00* (2013.01); *A61K 2039/53* (2013.01)

(58) Field of Classification Search
None
See application file for complete search history.

(56) References Cited

U.S. PATENT DOCUMENTS

| | | | |
|---|---|---|---|
| 5,962,224 A * | 10/1999 | Shin .................. | C07K 14/4702 435/320.1 |
| 6,291,645 B1 | 9/2001 | Shin et al. | |
| 6,544,948 B1 * | 4/2003 | Schweighoffer et al. ... | 514/19.3 |
| 2003/0232399 A1 | 12/2003 | Robertson et al. | |
| 2003/0235558 A1 * | 12/2003 | Shin .................. | C07K 14/4702 424/93.2 |

FOREIGN PATENT DOCUMENTS

WO        9220794 A1    11/1992

OTHER PUBLICATIONS

Ma et al. (Seminars in Immunology, 2010, 22:113-124).*
Machiels et al. (Cancer Research, 2001, 62:3689-3697).*
Alizadeh et al. (Cancer Research, 2013, 74:104-118).*
Chen et al. (PNAS, 2005, 102:13604-13609).*
Cao et al. (BMC Cancer, 2016, 16:343(p. 1-11)).*
Moscat et al., "The atypical PKC scaffold protein P62 is a novel target for anti-inflammatory and anti-cancer therapies", Advan. Enzyme Regul. 42, 2002, 173-179.
Twitty et al., Tumor-derived autophagosome vaccine: induction of cross-protective immune responses against short lived proteins through a p62-dependent mechanism. Clin. Chem. Res. 2011 17(20):6467-81.
International Preliminary Report on Patentability mailed on: Feb. 11, 2014 in International Application No. PCT/US2012/050024 filed on Aug. 8, 2012 and published as: WO/2013/022991 on: Feb. 14, 2013.
International Search Report mailed on: Feb. 1, 2013 in International Application No. PCT/US2012/050024 filed on Aug. 8, 2012 and published as: WO/2013/022991 on: Feb. 14, 2013.
Written Opinion mailed on: Feb. 1, 2013 in International Application No. PCT/US2012/050024 filed on Aug. 8, 2012 and published as: WO/2013/022991 on: Feb. 14, 2013.
Duran et al., "The signaling adaptor p62 is an important NF-kappaB mediator in tumorigenesis," Cancer Cell 13(4), 2011, 343-354.
Rolland et al., "The ubiquitin-binding protein p62 is expressed in breast cancers showing features of aggressive disease," Endocr. Relat. Cancer 14(1), 2007, 73-80.
Yu et al., "p62/SQSTMI involved in cisplatin resistance in human ovarian cancer cells by clearing ubiquitinated proteins", European Journal of Cancer 47, 2011, 1585-1594.
Thompson et al., "p62 overexpression in breast tumors and regulation by prostate-derived Ets factor in breast cancer cells," Oncogene 22, 2008, 2322-2333.

* cited by examiner

*Primary Examiner* — Julie Wu
(74) *Attorney, Agent, or Firm* — The Law Office of Leslie B. Overman

(57) ABSTRACT

Provided herein are novel p62 compositions for the prophylaxis and treatment of cancer and related methods. The invention also provides modified p62 compositions that increase the anti-cancer activity of p62.

14 Claims, 10 Drawing Sheets

```
   1 cctctcgagg cggggcgggg cctccgcgtt cgctacaaaa gccgcgcggc ggctgcgacc
  61 gggacggccc gttttccgcc agctcgccgc tcgctatggc gtcgctcacc gtgaaggcct
 121 accttctggg caagtaggac gcggcgcgcg agattcgccg cttcagcttc tgctgcagcc
 181 ccgagcctga ggcggaagcc gaggctgcgg cgggtccggg accctgcag gggtgctga
 241 gccgggtggc cgccctgttc cccgcgctgc ggcctggcgg cttccaggcg cactaccgcg
 301 atgaggacgg ggacttggtt gccttttcca gtgacgagga attgacaatg gccatgtcct
 361 acgtgaagga tgacatcttc cgaatctaca ttaaagagaa aaagagtgc cggcgggacc
 421 accgccacc gtgtgctcag gaggcgcccc gcaacatgt gcaccccaat gtgatctgcg
 481 atggctgcaa tgggcctgtg gtaggaaccc gctacaagtg cagcgtctgc ccagactacg
 541 acttgtgtag cgtctgcagg ggaaagggct tgcaccgggg gcacaccaag ctcgcattcc
 601 ccagcccctt cgggcacctg tctgagggct tctcgcacag ccgctggctc cggaaggtga
 661 aacacggaca cttcgggtgg ccaggatggg aaatgggtcc accaggaaac tggagcccac
 721 gtcctcctcg tgcagggag gcccgccctg gcccacggc agaatcagct tctggtccat
 781 cggaggatcc gagtgtgaat ttcctgaaga acgttgggga gagtgtggca gtgccctta
 841 gccctctggg cattgaagtt gatatcgatg tgagcacgg agggaaaaga agccgcctga
 901 ccccgtctc tccagagagt tcagcacag aggagaagag cagctcacag ccaagcagct
 961 gctgtctga ccccagcaag ccggtggga atgttgaggg cgccacgcag tctctgcgg
1021 agcagatgag gaagatcgcc ttggagtcg aggggcgccc tgaggaacag atggagtcgg
1081 ataactgttc aggagagat tatgactgga cccatctgtc ttcaaagaa gtggaccgt
1141 ctacaggtga actccagtcc ctacagatgc cagaatccga agggccaagc tctctggacc
1201 cctcccagga gggacccaca gggctgaagg aagctgcctt gtacccacat ctccgccag
1261 aggctgaccc ggggctgatt gagtccctct cccagatgct gtccatgggc ttctctgatg
1321 aaggcggctg gtcaccagg ctcctgcaga ccaagaacta tgacatcgga gggctctgg
1381 acaccatcca gtattcaaag catccccgc cgttgtgacc actttgccc acctcttctg
1441 cgtgccctc ttctgtctca tagttgtgtt aagcttgcgt agaattgcag gtctctgtac
1501 gggccagttt ctctgccttc ttccaggatc agggttagg gtgcaagaag ccatttaggg
1561 cagcaaaaca agtgacatga agggagggtc cctgtgtgtg tgtgctga tgtttcctgg
1621 gtgcctggc tccttgcago agggctggc ctgcgagacc caaggctcac tgcagcgcgc
1681 tcctgacccc tccctgcagg ggctacgtta gcagcccagc acatagcttg cctaatggct
1741 ttcactttct ctttgtttt aaatgactca taggtccctg acatttagtt gattatttc
1801 tgctacagac ctgtacact ctgatttag ataaagtaag cctaggtgtt gtcagcaggc
1861 aggctgggga ggccagtgtt gtgggcttcc tgctgggact gagaaggctc acgaaggca
1921 tccgcaatgt tggtttcact gagagctgcc tcctggtctc ttccaccactg tagttctctc
1981 atttccaaac catcagctgc tttaaaata agatctcttt gtagccatcc tgttaaattt
2041 gtaaacaatc taattaaatg gcatcagcac tttaaccaat gacgtttgca tagagagaaa
2101 tgattgacag taagtttatt gttaatggtt cttacagagt atctttaaaa gtgccttagg
2161 ggaaccctgt ccctcctaac aagtgtatct cgattaataa cctgccagtc ccagatcaca
2221 catcatcatc gaagtcttcc ccagttataa agaggtcaca tagtcgtgtg ggtcgaggat
2281 tctgtcctc caggaccagg ggccaccct ctgccaggg agtccttgcg tccatgagg
2341 tcttcccgca aggcctctca gaccagatg tgacggggtg tgtggcccga ggaagctgga
2401 cagcggcagt gggcctgctg aggccttcta ttgaggcctg tgctctgggg gtccttgct
2461 tagcctgtgc tggaccagct ggcctgggt ccctctgaag agaccttggc tgctcactgt
2521 ccacatgtga actttttcta ggtggcagga caattgcgc ccatttagag gatgtggctg
2581 taacctgctg gatgggactc catagctcct tccaggacc ctcagctcc ccggcactgc
2641 agtctgcaga gttctcctgg aggcagggc tgctgcttg tttcaccttc catgtcaggc
2701 cagcctgtcc ctgaaagaga agatggccat gccctccatg tgtaagaaca atgccaggc
2761 ccaggaggac cgcctgccct gcctggggct tggctgggcc tctggttctg acactttctg
2821 ctggaagctg tcaggctggg acaggctttg attttgaggg ttacaagac aaagcaaata
2881 aatgccttcc acctcaccgc aaaaaaaaaa aaaaaaaaaa aaa (SEQ ID NO: 1)
```

FIG. 1

```
  1 masltvkayl lqkedaarei rrfsfccspe peaeaeaaaq pqpcerllsr vaalfpalrp
 61 ggfqahyrde dgdlvafssd eeltmamsyv kddifrlyik ekkecrrdbr ppcaqeaprn
121 mvhpnvlcdg cngpvvgtry kcsvcpdydl csvcegkglh rghtklafps pfghlseqfs
181 barwlrkvkb ghfqwpgwem gppgowspxp pragearpgp taesasqpse dpsvoflknv
241 gesvaaalsp lglevdldve hggkrsritp vspessstee ksssqpsscc sdpskpggnv
301 egatqslaeq mrklalaseg rpeeqmesdn csgydddwtb lsskevdpst gelqslqmpe
361 segpssldps qegptglkea alyphlppea dprlleslaq mlsmgfsdeg gwltrllqtk
421 nydlgaaldt lqyskhpppl (SEQ ID NO: 2)
```

FIG. 2

→ Blood Spots

SEQUENCE LISTING

```
<160> NUMBER OF SEQ ID NOS: 4

<210> SEQ ID NO 1
<211> LENGTH: 2923
<212> TYPE: DNA
<213> ORGANISM: Homo sapiens

<400> SEQUENCE: 1
cctctcgagg cggggcgggg cctccgcgtt cgctacaaaa gccgcgcggc ggctgcgacc      60
gggacggccc gttttccgcc agctcgccgc tcgctatggc gtcgctcacc gtgaaggcct     120
accttctggg caaggaggac gcggcgcgcg agattcgccg cttcagcttc tgctgcagcc     180
ccgagcctga ggcggaagcc gaggctgcgg cgggtccggg accctgcgag cggctgctga     240
```

```
gccgggtggc cgccctgttc cccgcgctgc ggcctggcgg cttccaggcg cactaccgcg     300
atgaggacgg ggacttggtt gccttttcca gtgacgagga attgacaatg gccatgtcct     360
acgtgaagga tgacatcttc cgaatctaca ttaaagagaa aaaagagtgc cggcgggacc     420
accgcccacc gtgtgctcag gaggcgcccc gcaacatggt gcaccccaat gtgatctgcg     480
atggctgcaa tgggcctgtg gtaggaaccc gctacaagtg cagcgtctgc ccagactacg     540
acttgtgtag cgtctgcgag ggaaagggct gcaccgggg gcacaccaag ctcgcattcc      600
ccagccccct cgggcacctg tctgagggct tctcgcacag ccgctggctc cggaaggtga     660
aacacggaca cttcgggtgg ccaggatggg aaatgggtcc accaggaaac tggagcccac     720
gtcctcctcg tgcagggag gcccgccctg gcccacggc agaatcagct tctggtccat       780
cggaggatcc gagtgtgaat tcctgaaga cgttgggga gagtgtggca gctgcccttta      840
gccctctggg cattgaagtt gatatcgatg tggagcacga agggaaaaga agccgcctga     900
cccccgtctc tccagagagt tccagcacag aggagaagag cagctcacag ccaagcagct     960
gctgctctga cccagcaag ccgggtggga atgttgaggg cgccacgcag tctctggcgg     1020
agcagatgag gaagatcgcc ttggagtccg aggggcgccc tgaggaacag atggagtcgg    1080
ataactgttc aggaggagat gatgactgga cccatctgtc ttcaaaagaa gtggacccgt    1140
ctacaggtga actccagtcc ctacagatgc cagaatccga agggccaagc tctctggacc    1200
cctcccagga gggacccaca gggctgaagg aagctgcctt gtacccacat ctcccgccag    1260
aggctgaccc gcggctgatt gagtccctct cccagatgct gtccatgggc ttctctgatg    1320
aaggcggctg gctcaccagg ctcctgcaga ccaagaacta tgacatcgga gcggctctgg    1380
acaccatcca gtattcaaag catccccgc cgttgtgacc acttttgccc acctcttctg     1440
cgtgcccctc ttctgtctca tagttgtgtt aagcttgcgt agaattgcag gtctctgtac    1500
gggccagttt ctctgccttc ttccaggatc aggggttagg gtgcaagaag ccatttaggg    1560
cagcaaaaca agtgacatga agggagggtc cctgtgtgtg tgtgtgctga tgtttcctgg    1620
gtgccctggc tccttgcagc agggctgggc ctgcgagacc caaggctcac tgcagcgcgc    1680
tcctgacccc tccctgcagg ggctacgtta gcagcccagc acatagcttg cctaatgggct   1740
ttcactttct cttttgtttt aaatgactca taggtccctg acatttagtt gattattttc    1800
tgctacagac ctggtacact ctgatttag ataaagtaag cctaggtgtt gtcagcaggc     1860
aggctgggga ggccagtgtt gtgggcttcc tgctgggact gagaaggctc acgaagggca    1920
tccgcaatgt tggtttcact gagagctgcc tcctggtctc ttcaccactg tagttctctc    1980
atttccaaac catcagctgc ttttaaaata agatctcttt gtagccatcc tgttaaattt    2040
gtaaacaatc taattaaatg gcatcagcac tttaaccaat gacgtttgca tagagagaaa    2100
tgattgacag taagtttatt gttaatggtt cttacagagt atctttaaaa gtgccttagg    2160
ggaaccctgt ccctcctaac aagtgtatct cgattaataa cctgccagtc ccagatcaca    2220
catcatcatc gaagtcttcc ccagttataa agaggtcaca tagtcgtgtg ggtcgaggat    2280
tctgtgcctc caggaccagg ggcccaccct ctgcccaggg agtccttgcg tcccatgagg    2340
tcttcccgca aggcctctca gacccagatg tgacggggtg tgtggcccga ggaagctgga    2400
cagcggcagt gggcctgctg aggccttctc ttgaggcctg tgctctgggg gtcccttgct    2460
tagcctgtgc tggaccagct ggctgggggt ccctctgaag agaccttggc tgctcactgt    2520
ccacatgtga acttttttcta ggtggcagga caaattgcgc ccatttagag gatgtggctg   2580
taacctgctg gatgggactc catagctcct tcccaggacc cctcagctcc ccggcactgc    2640
```

-continued

```
agtctgcaga gttctcctgg aggcagggc tgctgccttg tttcaccttc catgtcaggc    2700
cagcctgtcc ctgaaagaga agatggccat gccctccatg tgtaagaaca atgccagggc    2760
ccaggaggac cgcctgccct gcctgggcct tggctgggcc tctggttctg cactttctg    2820 ctggaagctg tcaggctggg acaggctttg attttgaggg ttagcaagac aaagcaaata    2880
aatgccttcc acctcaccgc aaaaaaaaaa aaaaaaaaa aaa                       2923
```

<210> SEQ ID NO 2
<211> LENGTH: 440
<212> TYPE: PRT
<213> ORGANISM: Homo sapiens

<400> SEQUENCE: 2

```
Met Ala Ser Leu Thr Val Lys Ala Tyr Leu Leu Gly Lys Glu Asp Ala
1               5                   10                  15

Ala Arg Glu Ile Arg Arg Phe Ser Phe Cys Cys Ser Pro Glu Pro Glu
                20                  25                  30

Ala Glu Ala Glu Ala Ala Gly Pro Gly Pro Cys Glu Arg Leu Leu
            35                  40                  45

Ser Arg Val Ala Ala Leu Phe Pro Ala Leu Arg Pro Gly Gly Phe Gln
50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
                85                  90                  95

Ile Tyr Ile Lys Glu Lys Lys Glu Cys Arg Arg Asp His Arg Pro Pro
            100                 105                 110

Cys Ala Gln Glu Ala Pro Arg Asn Met Val His Pro Asn Val Ile Cys
        115                 120                 125

Asp Gly Cys Asn Gly Pro Val Val Gly Thr Arg Tyr Lys Cys Ser Val
130                 135                 140

Cys Pro Asp Tyr Asp Leu Cys Ser Val Cys Glu Gly Lys Gly Leu His
145                 150                 155                 160

Arg Gly His Thr Lys Leu Ala Phe Pro Ser Pro Phe Gly His Leu Ser
                165                 170                 175

Glu Gly Phe Ser His Ser Arg Trp Leu Arg Lys Val Lys His Gly His
            180                 185                 190

Phe Gly Trp Pro Gly Trp Glu Met Gly Pro Pro Gly Asn Trp Ser Pro
        195                 200                 205

Arg Pro Pro Arg Ala Gly Glu Ala Arg Pro Gly Pro Thr Ala Glu Ser
210                 215                 220

Ala Ser Gly Pro Ser Glu Asp Pro Ser Val Asn Phe Leu Lys Asn Val
225                 230                 235                 240

Gly Glu Ser Val Ala Ala Leu Ser Pro Leu Gly Ile Glu Val Asp
                245                 250                 255

Ile Asp Val Glu His Gly Gly Lys Arg Ser Arg Leu Thr Pro Val Ser
            260                 265                 270

Pro Glu Ser Ser Ser Thr Glu Glu Lys Ser Ser Ser Gln Pro Ser Ser
        275                 280                 285

Cys Cys Ser Asp Pro Ser Lys Pro Gly Gly Asn Val Glu Gly Ala Thr
290                 295                 300

Gln Ser Leu Ala Glu Gln Met Arg Lys Ile Ala Leu Glu Ser Glu Gly
305                 310                 315                 320
```

```
Arg Pro Glu Glu Gln Met Glu Ser Asp Asn Cys Ser Gly Gly Asp Asp
                    325                 330                 335

Asp Trp Thr His Leu Ser Ser Lys Glu Val Asp Pro Ser Thr Gly Glu
                340                 345                 350

Leu Gln Ser Leu Gln Met Pro Glu Ser Glu Gly Pro Ser Ser Leu Asp
            355                 360                 365

Pro Ser Gln Glu Gly Pro Thr Gly Leu Lys Glu Ala Ala Leu Tyr Pro
        370                 375                 380

His Leu Pro Pro Glu Ala Asp Pro Arg Leu Ile Glu Ser Leu Ser Gln
385                 390                 395                 400

Met Leu Ser Met Gly Phe Ser Asp Glu Gly Gly Trp Leu Thr Arg Leu
                405                 410                 415

Leu Gln Thr Lys Asn Tyr Asp Ile Gly Ala Ala Leu Asp Thr Ile Gln
                420                 425                 430

Tyr Ser Lys His Pro Pro Pro Leu
                435                 440

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cccgctagca tggcgtcgct caccgtg                                          27

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cccaagcttt cacaacggcg ggggatgctt tg                                    32
```

METHODS AND COMPOSITIONS RELATING TO P62 FOR THE TREATMENT AND PROPHYLAXIS OF CANCER

CROSS-REFERENCE TO RELATED PATENT APPLICATIONS

This application is a 35 U.S.C. Section 371 National Stage Entry of International Application PCT/US2012/050024, filed Aug. 8, 2012, entitled "Methods and Compositions Relating to P62 for the Treatment and Prophylaxis of Cancer" which claims the benefit of U.S. Provisional Application Ser. No. 61/521,280 filed, Aug. 8, 2011, entitled "P62 as an Anti-Cancer Agent", which are incorporated herein by reference in their entirety and for all purposes.

SEQUENCE LISTING

The instant application contains a Sequence Listing which has been submitted electronically in ASCII format and is hereby incorporated by reference in its entirety. Said ASCII copy, created on Jul. 13, 2016, is named 151-00100_US_S-L.txt and is 8,516 bytes in size.

FIELD OF THE INVENTION

This invention relates generally to the field of cancer prevention and treatment. More specifically, the invention relates to cancer prevention and treatment by means of activating anti-cancer response using p62 compositions.

BACKGROUND OF THE INVENTION

Cancer is the second most common cause of death in the United States and European Union (National Vital Statistics Reports, Vol. 60, No. 4, 2012) and the first most common cause of death among persons aged 45 to 64, for both men and women, in the European Union. The estimated cancer prevalence in the United States as of Jan. 1, 2008 was 5,506,000 cases of invasive tumors for males and 6,452,000 cases for females.

Cancer vaccines are under investigation, with some in Phase III efficacy studies (Rosenberg et al., Nat Med., 10:909 (2004), Johnson et al., Expert Rev Anticancer Ther., 9:67 (2009)3,4). Several cancer vaccines are directed against solid tumors—melanoma, prostate, lung, breast and colorectal cancers. Two high risk populations will particularly benefit from preventive anti-cancer vaccines: the patients with surgically removed tumors belonging to cancer types that are known to have high metastatic potential (e.g., ovarian or some types of breast cancer), and also carriers of known mutations, associated with higher cancer risk (e.g., mutations in BRCA1 and BRCA2 genes for breast and ovarian cancers, RAD51 gene for ovarian cancer, etc.). Selective preventive vaccination of high-risk cohort of women is an important public health task.

p62 is a multifunctional protein that binds ubiquitin and regulates activation of the nuclear factor kappa-B (NF-kB) signaling pathway. The protein functions as a scaffolding/adaptor protein in concert with TNF receptor-associated factor 6 to mediate activation of NF-kB in response to upstream signals. Alternatively spliced transcript variants encoding either the same or different isoforms have been identified for this gene.

p62 was identified as 62-kDa protein that was binding the src homology 2 (SH2) domain of tyrosine kinase Lckp56 in a phosphotyrosine-independent manner (Park et al., Proc Natl Acad Sci USA., 92:12338 (1995)). The primary sequence of p62 is known (Joung et al., Proc Natl Acad Sci USA., 93:5991, (1996)), and was shown to bind ubiquitin (Vadlamudi et al., J. Biol. Chem., 271:20235 (1996)). The DNA sequence of human p62, *Homo sapiens* sequestosome 1 (SQSTM1), transcript variant 1, mRNA, can be accessed at NCBI Reference Sequence: NM_003900.4. The amino acid sequence of human p62, Sequestosome-1 isoform 1 [*Homo sapiens*], can be accessed at NCBI Reference Sequence: NP 003891.1. p62 has homology neither with ubiquitin C-terminal hydrolases nor with the S5a subunit of the 26 S proteasome complex, the only proteins known to bind to ubiquitin noncovalently. These results suggested that p62 belongs to a new class of ubiquitin-binding proteins.

p62 is a component of inclusion bodies found in protein aggregation diseases in the brain and liver: p62 is sequestered into cytoplasmic inclusion bodies, called sequestosomes. These p62-containing protein aggregates are degraded by autophagy. It was suggested that this function of p62 may have a protective effect on huntingtin-induced cell death (Bjorkoy et al., J Cell Biol., 171:603 (2005)). Mutations in p62 gene have been associated with sporadic and familial Paget disease (Jenny Chung et al., Semin Arthritis Rheum., 41:619 (2012)), a metabolic bone disease.

SUMMARY OF THE INVENTION

Provided herein are methods to treat, alleviate, ameliorate, relieve, delay onset of, inhibit progression of, reduce severity of, and/or reduce incidence of one or more symptoms of a cancer in a subject by administering to the subject an agent having (a) a p62 polypeptide or (b) a p62 encoding nucleic acid. The agent can have (a) one or more domain deletions, (b) a p62 encoding nucleic acid that is at least 95% identical to SEQ ID NO. 1, or (c) a p62 polypeptide that is at least 98% identical to SEQ ID NO: 2. The method domain deletions can be one or more of the following: PB1, ZZ, NLS2, TB, NLS1, NES, LIR, KIR, and UBA. The method can use a fusion polypeptide or nucleic acid encoding for a fusion polypeptide, respectively. The method can use a p62 polypeptide that is post-translationally modified.

The agent can be administered by any of the following routes: parenterally, orally, nasally, rectally, transdermally, intravaginally or inhalationally via an aerosol. The parenteral routes can be any of the following: intravascularly, intravenously, intraarterially, intramuscularly, intraocularly, intraperitoneally, intradermally and subcutaneously, or can be administered to an organ or to a tumor. The method can further include any and all of the following: administering of adjuvants, administering of co-stimulatory components, administering one or more molecules that block suppressive or negative regulatory immune mechanisms, or administering one or more anticancer therapies to said subject.

The method can be used to treat any cancer in a subject including: breast cancer, lung cancer, prostate cancer, gastric cancer, colorectal cancer, skin cancer, a cancer of the head and neck, bronchus cancer, pancreatic cancer, urinary bladder cancer, brain cancer, central nervous system cancer, peripheral nervous system cancer, esophageal cancer, cancer of the oral cavity or pharynx, liver cancer, kidney cancer, testicular cancer, biliary tract cancer, small bowel or appendix cancer, ovarian cancer, uterine cancer, salivary gland cancer, thyroid gland cancer, adrenal gland cancer, osteosarcoma, chondrosarcoma, sarcoma and cancer of hematological tissues. The subject can be: a subject diagnosed with cancer, a subject previously treated for cancer, a subject with a family history of cancer, or a subject predisposed to cancer.

The method can include an agent that is a p62 encoding nucleic acid and the nucleic acid can be included in a plasmid or a viral vector. The method can also include a strategy for improving the efficiency of nucleic acid-based immunization.

Also provided herein are agents to treat, alleviate, ameliorate, relieve, delay onset of, inhibit progression of, reduce severity of, and/or reduce incidence of one or more symptoms of a cancer in a subject that are a p62 polypeptide or a p62 encoding nucleic acid, having at least one or more domain deletions, or composed of one or more domains of a p62 polypeptide or a nucleic acid encoding one or more domains of a p62. The one or more domain can be among the following: PB1, ZZ, NLS2, TB, NLS1, NES, LIR, KIR, and UBA.

The agent can include a fusion polypeptide or encoding nucleic acid, respectively. The p62 polypeptide can be post-translationally modified.

The agent can further include one or more adjuvants, one or more co-stimulatory components, or one or more molecules that block suppressive or negative regulatory immune mechanisms, one or more chemotherapeutic molecules or an anti-angiogenic molecules.

The agent can be a p62 encoding nucleic acid further that is a component of a plasmid or a viral vector.

Provided herein are also compositions including the agent suitable for administration to a subject.

BRIEF DESCRIPTION OF THE DRAWINGS

FIG. 1 shows a wild type nucleic acid sequence of human p62 (SEQ ID NO: 1).

FIG. 2 shows a wild type amino acid sequence of the human p62 encoded by the nucleic acid sequence (SEQ ID NO: 2).

DETAILED DESCRIPTION OF THE INVENTION

Provided herein are p62 compositions and methods for treatment of cancer. While not wishing to be held by theory, the inventors have found that by administering p62 encoding nucleic acid to a subject the host immune defense mechanism is stimulated to attack neoplastic cells. Consequently DNA vaccines encoding a p62 polypeptide, or, p62 polypeptides, administered to a subject can stimulate an anticancer immune response.

As used herein, "p62 polypeptide" means a polypeptide corresponding to the full length p62/SQSTM1 protein. The term includes all homologs, analogs, fragments or derivatives of the p62/SQSTM1 protein. In one embodiment, the isolated p62 polypeptide has an amino acid sequence as shown in FIG. 2 (SEQ ID NO: 2). A "p62 encoding nucleic acid" means a DNA or RNA that encodes a p62 polypeptide.

In some embodiments, the subject is a human. In other embodiments, the subject is a non-human mammal, e.g., a horse, cow, sheep, pig, deer, dog, cat, rat, or a mouse.

In addition to the full length amino acid sequence, the polypeptides of the present invention may also include fragments or truncations, analogs, and homologs of the p62 polypeptide and truncations thereof as described herein. Fragments can include peptides of at least 5, at least 10, at least 15, at least 20, at least 25 or at least 30 amino acid residues of the full length polypeptide.

Deletions of one or more amino acids, or discrete portions from the amino acid sequence of the p62/SQSTM1 protein are also included. The deleted amino acids may or may not be contiguous. The lower limit. length of the resulting analog with a deletion mutation is about 10, about 20, about 50, or about 100 amino acids.

Figure 3:
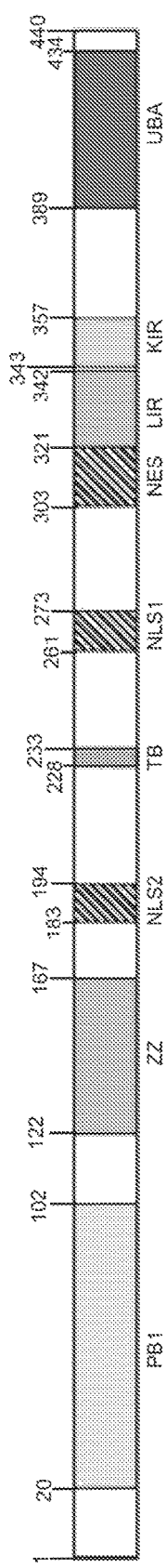
FIG. 3 shows a cartoon of the domain structure of human p62.

In some embodiments, the p62 polypeptide has one or more deleted domains. While not wishing to be held by theory, the inventors hold that the deletion of one or more domains of the p62 polypeptide provide a more compact and manipulable polypeptide for directing an immune response. For example, by disrupting or eliminating one or more of the domains of a p62 polypeptide, immunogenicity can be retained (or improved if the deleted or disrupted domain does not contribute to immunogenicity) in a more compact molecule and potentially increase the number of epitopes presented to host antibodies on a per weight basis. In addition, removal or reordering of domains responsible for engagement with other cellular processes or its own intra-cellular protein degradation can improve its anticancer effect. The p62 polypeptide has a domain structure as provided in Table 1 below and as shown in FIG. 3:

TABLE 1

| | p62 Polypeptide Domain Structure |

| Domain/site | Full name | Location | Description |
|---|---|---|---|
| PB1 | Phox/Bem1p domain (=OPR domain) | 20-102 | PB1-domain is conserved among eukaryotes (protista, plants, fungi and animals). PB1-domain has specific - ubiquitin-like β-grasp fold. There are 3 types of PB1-domains: type I domains contains acid OPCA-motif, type II domains contain conservative Lys residue in the first β-sheet, and I/II type domains contain both of the above. OPCA-motif can bind to basic amino acids (e.g., lysine) via salt bridges, enabling ability of PB1-domains to form heteromeric structures (Sumimoto et al., 2007Sci STKE., 401: 6 (2007)). PB1-domain of p62 is type I/II (Lamark et al., 2003 J Biol Chem., 278: 34568 (2003)). PB1-domain is responsible for di- and multimerization of p62, as well as interaction with other proteins: MEKK3, MEK5, PKCζ, PKCλ/ι (protein kinases containing PB1-domain), NBR1 (Next to BRCA1, contains PB1-domain) (Nezis, Stenmark, 2011Antioxid Redox Signal., 17: 786 (2011)). |
| ZZ | Zn2+-finger ZZ type | 122-167 | ZZ-domain is $Zn^{2+}$-finger of C2H2 type. ZZ-domain of p62 binds to RIP1 (receptor interacting protein 1). RIP1 is a regulatory protein kinase which integrates signaling pathways activated by bacterial or viral infection (via PAMP), death receptors, or genotoxins; it takes part in determination of cell fate (survival, apoptosis, or necrosis) (Festjens et al., Cell Death Differ., 14: 400 (2007)). |
| NLS2 | Nuclear localization signal 2 | 183-194 | Tentative nuclear localization signal (Pankiv et al., J Biol Chem., 285: 5941 (2009)) |
| TB | TRAF6-binding domain | 228-233 | p62 binds via TB domain to E3-ubiquitin protein ligase TRAF6. TRAF6 activates kinase TAK1, polyubiqitinating it via K63). TRAF6 participates in signaling from RANK-L, IL-1R, TCR, BCR and TGFβ receptors (Landström, Int J Biochem Cell Biol., 42: 585 (2010)). Interaction of p62 with TRAF6 stimulates autoubiqitination of TRAF6 n E3- ligase activity. This process requires PB1- and UBA-domains (Moscat et al., Mol Cell., 23: 631 (2006)). |
| NLS1 | Nuclear localization signal 1 | 261-273 | Tentative nuclear localization signal (Pankiv et al., 2009) |
| NES | Nuclear export signal | 303-321 | Tentative nuclear export signal (Pankiv et al., 2009) |
| LIR | LC3 interaction region | 321-342 | LIR-domain is required for binding of p62 to LC3 protein (wild-type human microtubule-associated protein 1 light chain 3, Light Chain 3) (Pankiv et al., J Biol Chem., 282: 24131 (2007)LC3 -ubiquitin-like protein, conjugating with phosphatidyl ethanolamine of autophagosome membrane (Tanida, Microbiol Immunol., 55: 1 (2011)). P62 via interaction of with LC3, p62 is recruited to autophagosomes (Shvets et al., Autophagy, 7: 683 (2011)), apparently transporting ubiquitinated proteins associated with UBA domain. |
| KIR | Keap1 interaction region | 343-357 | KIR domain is required for interaction with DC domain of Keap1 protein, containing Kelch repeats (Komatsu et al., Nat Cell Biol., 12: 213 (2010)). Keap1 (Kelch-like ECH-associated protein 1) is a regulator of activity of transcription factor Nrf2 (NF-E2-related factor 2). Nrf2 regulates expression of genes involved in glutathione synthesis, ROS detoxification, metabolism of xenobiotics and drug transport (Taguchi et al., Genes Cells, 16: 123 (2011)). Overexpression of p62 displaces Nrf2 from Keap1, Nrf2 is stabilized which lead to stimulation of expression of Nrf2-dependent genes. Paradoxically, hyperactivation of Nrf2 and overexpression of genes considered "cytoprotective" causes severe pathology (Komatsu et al., 2010). |
| UBA | Ubiquitin-associated domain | 389-434 | UBA-domain is one of domains which can bind to polyubiquitinated labels (along with CUE, UIM, NZF etc.). UBA-domains can be divided in four classes depending on their ability to bind polyubiquitin labels of different structures (K6, K29, K48, K63). UBA-domain of p62 belongs to class 4, which consists of domains with equal affinity for binding to K6, K29, K48, K63 (Raasi et al., Nat Struct Mol Biol., 12: 708 (2005)). UBA domain also participates in p62 dimerization (Garner et al., Biochemistry, 50: 9076 (2011)). Most of mutations associated with Paget disease are localized in UBA domain (Yan Jenny Chung, Van Hul, Semin Arthritis Rheum, 4: 619 (2011)). However, p62 mutations are not enough for osteoblasts to acquire the |

TABLE 1-continued p62 Polypeptide Domain Structure

| Domain/site | Full name | Location | Description |
|---|---|---|---|
| | | | specific Paget phenotype: The expression of nucleocapsid protein of measles virus is also required (Singer, Cell Metab., 13: 5 (2011)). The structure of UBA domain is well studied (Isogai et al., J Biol Chem, 286: 31864 (2011)). |

Sequence numeration: NP_003891 (sequestosome-1 isoform 1 [*Homo sapiens*]).

In some embodiments, one or more of the above domains are deleted from a p62 polypeptide at corresponding codons for the nucleic acid regions of the p62 nucleic acid (in-frame deletions), as presented below in Table 2.

TABLE 2

Deletions in p62

| Deleted domain | Start of the deletion, between nts | End of the deletion, between nts |
|---|---|---|
| PB1 | 1 and 20 | 102 and 122 |
| ZZ | 102 and 122 | 167 and 183 |
| NLS2 | 167 and 183 | 194 and 228 |
| TB | 194 and 228 | 233 and 261 |
| NLS1 | 233 and 261 | 273 and 303 |
| NES-LIR-KIR | 273 and 303 | 357 and 389 |
| UBA | Stop codon between 357 and 389 | Not applicable |

Nucleotide numbers refer to p62 NCBI reference sequence NP_003891 (sequestosome-1 isoform 1 [*Homo sapiens*]).

For example, any deletion of the encoding nucleic acid sequence that starts at nucleotide 102 up to nucleotide 122 and ends at 167 up to 183 is considered a ZZ deletion. Therefore, e.g. a 110-175 is a ZZ deletion. Techniques for creating in-frame deletions are well known to those skilled in the art.

In some embodiments, the p62 polypeptide (or the p62 polypeptide encoded by a nucleic acid) is composed of one or more of the above domains. In some embodiments, the p62 polypeptide (or the p62 polypeptide encoded by a nucleic acid) is composed of two or more of the above domains and still further embodiments, the domains are the compose the polypeptide are in a different N-terminal to C-terminal order than that presented in the wild type p62 polypeptide.

As used herein, "biologically active or immunologically active" refers to polypeptides according to the present invention having a similar structural function (but not necessarily to the same degree), and/or similar regulatory function (but not necessarily to the same degree), and/or similar biochemical function (but not necessarily to the same degree) and/or immunological activity (but not necessarily to the same degree) as the individual wild type polypeptides.

As used herein, a "deletion" is defined as a change in amino acid sequence in which one or more amino acid residues are absent as compared to the wild-type protein.

As used herein an "insertion" or "addition" is a change in an amino acid sequence that has resulted in the addition of one or more amino acid residues as compared to the wild-type protein.

As used herein "substitution" results from the replacement of one or more amino acids by different amino acids, respectively, as compared to the wild-type protein. In some embodiments, the substitution mutation is C145R or Q418R.

As used herein, the term "variant" means any polypeptide having a substitution of, deletion of or addition of one (or more) amino acid from or to the sequence (or any combination of these), including allelic variations, as compared with the wild-type protein, so long as the resultant protein retains at least 75%, at least 80%, at least 85%, at least 90%, at least 95%, or at least 99% of the immunogenic activity as compared to the wild-type proteins as used in the present invention. Typically, variants of the polypeptides embraced by the present invention will have at least 80%, at least 85%, at least 90%, at least 91%, at least 92%, at least 93%, at least 94%, at least 95%, at least 96%, at least 97%, at least 98%, or at least 99% sequence identity to SEQ. ID. NO. 2.

Sequence identity or homology can be determined using standard techniques known in the art, such as the Best Fit sequence program described by Devereux et al., Nucl. Acid Res. 12; 387-395 (1984) or the BLASTX program (Altschul et al., J Mol. Biol. 215, 403-410). The alignment may include the introduction of gaps in the sequences to be aligned. In addition, for sequences which contain either more or fewer amino acids than the proteins disclosed herein, it is understood that the percentage of homology will be determined based on the number of homologous amino acids in relation to the total number of amino acids.

In some embodiments, variants or derivatives of the polypeptides of the present invention maintain the hydrophobicity/hydrophilicity of the amino acid sequence. Conservative amino acid substitutions may be made, for example from 1, 2 or 3 to 10, 20 or 30 substitutions provided that the modified sequence retains the ability to act as an immunogen in accordance with present invention. Amino acid substitutions may include the use of non-naturally occurring analogues, for example to increase blood plasma half-life. Conservative substitutions are known in the art The term "derivative" as used herein in relation to the amino acid sequence means chemical modification of a polypeptide of the invention.

Non-limiting examples of such modifications may include but are not limited to aliphatic esters or amides of the carboxyl terminus or of residues containing carboxyl side chains, O-acyl derivatives of hydroxyl group-containing residues, and N-acyl derivatives of the amino-terminal amino acid or amino-group containing residues, e.g., lysine or arginine.

Additional modifications can include, for example, production of a polypeptide conjugated with polyethylene glycol (PEG), or addition of PEG during chemical synthesis of a polypeptide of the invention.

Modifications of polypeptides or portions thereof can also include reduction/alkylation; chemical coupling to an appropriate carrier or mild formalin treatment.

The term "modified," as used herein refers to the presence of a post-translational modification on a polypeptide. The form "(modified)" term means that the polypeptides being discussed are optionally modified, that is, the polypeptides under discussion can be modified or unmodified.

The term "post-translationally modified" and "modified" refers to any modification of a natural or non-natural amino acid that occurs to such an amino acid after it has been incorporated into a polypeptide chain. The term encompasses, by way of example only, co-translational in vivo modifications, post-translational in vivo modifications, and post-translational in vitro modifications.

Other derivatives of the polypeptides of the present invention include incorporation of unnatural amino acid residues, or phosphorylated amino acid residues such as phosphotyrosine, phosphoserine or phosphothreonine residues. Other potential modifications include sulfonation, biotinylation, or the addition of other moieties, particularly those which have molecular shapes similar to phosphate groups.

Derivatives also include polypeptides modified by glycosylation. These can be made by modifying glycosylation patterns during synthesis and processing in various alternative eukaryotic host expression systems, or during further processing steps. Methods for producing glycosylation modifications include exposing the p62 polypeptide to glycosylating enzymes derived from cells that normally carry out such processing, such as mammalian glycosylation enzymes. Alternatively, deglycosylation enzymes can be used to remove carbohydrates attached during production in eukaryotic expression systems. Additionally, one can also modify the coding sequence so that glycosylations site(s) are added or glycosylation sites are deleted or disabled. Furthermore, if no glycosylation is desired, the proteins can be produced in a prokaryotic host expression system.

Variants and/or derivatives of the polypeptides of the invention can be prepared by chemical synthesis or by using site-directed mutagenesis (Gillman et al., Gene 8:81 (1979); Roberts et at, Nature 328:731 (1987) or Innis (Ed.), 1990, PCR Protocols: A Guide to Methods and Applications, Academic Press, New York, N.Y.) or the polymerase chain reaction method (PCR; Saiki et al, Science 239:487 (1988)), as exemplified by Daugherty et at (Nucleic Acids Res. 19:2471 (1991)) to modify nucleic acids encoding the p62 polypeptides of the invention.

In another embodiment a polypeptides of the present invention may contain a heterologous signal sequence at its N-terminus. In certain host cells (e.g., mammalian host cells), expression and/or secretion of the fusion protein can be increased through use of a heterologous signal sequence. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products).

In order to enhance stability and/or reactivity, the polypeptides of the present invention can also be modified to incorporate one or more polymorphisms in the amino acid sequence resulting from natural allelic variation. Additionally, D-amino acids, non-natural amino acids or non-amino acid analogues can be substituted or added to produce a modified p62 polypeptide within the scope of this invention.

The polypeptides of the present invention may be produced by expression of a nucleotide sequence coding for same in a suitable expression system.

In addition, or in the alternative, the polypeptides can be produced using chemical methods to synthesize the desired amino acid sequence, in whole or in part. For example, polypeptides can be synthesized by solid phase techniques, cleaved from the resin, and purified by preparative high performance liquid chromatography (e.g., Creighton (1983) Proteins Structures And Molecular Principles, WH Freeman and Co, New York N.Y.). The composition of the synthetic polypeptides may be confirmed by amino acid analysis or sequencing (e.g., the Edman degradation procedure). Additionally, the amino acid sequence of a p62 polypeptide, or any part thereof, may be altered during direct synthesis and/or combined using chemical methods with a sequence from other subunits, or any part thereof, to produce a variant polypeptide.

Assays for measuring the immunologic activity of any homolog, derivative or variant of any polypeptides of the present invention are well known in the art.

As used herein, the term "fusion proteins" refers to chimeric proteins comprising amino acid sequences of two or more different proteins. Typically, fusion proteins result from in vitro recombinatory techniques well known in the art.

In additional embodiments, the fusion proteins of the present invention may further comprise one or more additional polypeptide domains added to facilitate protein purification, to increase expression of the recombinant protein, or to increase the solubility of the recombinant protein. Such purification/expression/solubility facilitating domains include, but are not limited to, metal chelating peptides such as histidine-tryptophan modules that allow purification on immobilized metals (Porath J (1992) Protein Expr Purif 3-.26328 1), protein A domains that allow purification on immobilized immunoglobulin, and the domain utilised in the FLAGS extension/affinity purification system (Immunex Corp, Seattle, Wash.). The inclusion of a cleavable linker sequence such as Factor Xa or enterokinase (Invitrogen, San Diego, Calif.) between the purification domain and a p62 polypeptide is useful to facilitate purification.

Additional fusion expression vectors include pGEX (Pharmaci, a Piscataway, N.J.), pMAL (New England Biolabs, Beverly, Mass.) and pRITS (Pharmacia, Piscataway, N.J.) which fuse glutathione S transferase (GST), maltose B binding protein, or protein A, respectively, to the target recombinant protein. EBV, BKV, and other episomal expression vectors (Invitrogen) can also be used In certain embodiments, a nucleic acid molecule encoding p62 polypeptide is utilized. The nucleic acid molecule may comprise or consist of a nucleotide sequence encoding one or more p62 polypeptides, or fragments (including fragments that code for domains in any order or polypeptides wherein one or more domains are deleted or disrupted) or derivatives thereof, such as that contained in a DNA insert in an ATCC Deposit. The term "nucleic acid sequence" or "nucleic acid molecule" refers to a DNA or RNA sequence. The term encompasses molecules formed from any of the known base analogs of DNA and RNA such as, but not limited- to 4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5' methoxycarbonylmethyluracil, 5-methoxyuracil, 2-methylthio-N6-isopentenyladenine, uracil-5-oxyacetic acid methylester, uracil-5- oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine, among others.

In certain embodiments of the present invention, vectors are used to transfer a nucleic acid sequence encoding a polypeptide to a cell. A vector is any molecule used to transfer a nucleic acid sequence to a host cell. In certain cases, an expression vector is utilized. An expression vector is a nucleic acid molecule that is suitable for introduction to and/or propagation in a host cell and contains nucleic acid sequences that direct and/or control the expression of the transferred nucleic acid sequences. Expression includes, but is not limited to, processes such as transcription, translation, and splicing, if introns are present. Expression vectors typically comprise one or more flanking sequences operably linked to a heterologous nucleic acid sequence encoding a polypeptide. Flanking sequences may be homologous (i.e., from the same species and/or strain as the host cell), heterologous (i.e., from a species other than the host cell species or strain), hybrid (i.e., a combination of flanking sequences from more than one source), or synthetic, for example.

A flanking sequence is preferably capable of effecting the replication, transcription and/or translation of the coding sequence and is operably linked to a coding sequence. As used herein, the term operably linked refers to a linkage of polynucleotide elements in a functional relationship. For instance, a promoter or enhancer is operably linked to a coding sequence if it affects the transcription of the coding sequence. However, a flanking sequence need not necessarily be contiguous with the coding sequence, so long as it functions correctly. Thus, for example, intervening untranslated yet transcribed sequences can be present between a promoter sequence and the coding sequence and the promoter sequence may still be considered operably linked to the coding sequence. Similarly, an enhancer sequence may be located upstream or downstream from the coding sequence and affect transcription of the sequence.

In certain embodiments, it is preferred that the flanking sequence is a transcriptional regulatory region that drives high-level gene expression in the target cell. The transcriptional regulatory region may comprise, for example, a promoter, enhancer, silencer, repressor element, or combinations thereof. The transcriptional regulatory region may be either constitutive, tissue-specific, cell-type specific (i.e., the region is drives higher levels of transcription in a one type of tissue or cell as compared to another), or regulatable (i.e., responsive to interaction with a molecule). The source of a transcriptional regulatory region may be any prokaryotic or eukaryotic organism, any vertebrate or invertebrate organism, or any plant, provided that the flanking sequence functions in a cell by causing transcription of a nucleic acid within that cell. A wide variety of transcriptional regulatory regions may be utilized in practicing the present invention.

Suitable transcriptional regulatory regions include, for example, the CMV promoter (i.e., the CMV-immediate early promoter); promoters from eukaryotic genes (i.e., the estrogen-inducible chicken ovalbumin gene, the interferon genes, the gluco-corticoid-inducible tyrosine aminotransferase gene, and the thymidine kinase gene); and the major early and late adenovirus gene promoters; the SV40 early promoter region (Bernoist and Chambon, 1981, Nature 290: 304-10); the promoter contained in the 3' long terminal repeat (LTR) of Rous sarcoma virus (RSV) (Yamamoto, et al., 1980, Cell 22:787-97); the herpes simplex virus thymidine kinase (HSV-TK) promoter (Wagner et al., 1981, Proc. Natl. Acad. Sci. U.S.A. 78:1444-45); the regulatory sequences of the metallothionine gene (Brinster et al., 1982, Nature 296:39-42); prokaryotic expression vectors such as the beta-lactamase promoter (VIIIa-Kamaroff et al., 1978, Proc. Natl. Acad. Sci. U.S.A., 75:3727-31); or the tac promoter (DeBoer et al., 1983, Proc. Natl. Acad. Sci. U.S.A., 80:21-25). Tissue- and/or cell-type specific transcriptional control regions include, for example, the elastase I gene control region which is active in pancreatic acinar cells (Swift et al., 1984, Cell 38:639-46; Ornitz et al., 1986, Cold Spring Harbor Symp. Quant. Biol. 50:399-409 (1986); MacDonald, 1987, Hepalology 7:425-515); the insulin gene control region which is active in pancreatic beta cells (Hanahan, 1985, Nature 315:115-22); the immunoglobulin gene control region which is active in lymphoid cells (Grosschedl et al., 1984, Cell 38:647-58; Adames et al., 1985, Nature 318:533-38; Alexander et al., 1987, Mol. Cell. Biol., 7:1436-44); the mouse mammary tumor virus control region in testicular, breast, lymphoid and mast cells (Leder et al., 1986, Cell 45:485-95); the albumin gene control region, in liver (Pinkert et al., 1987, Genes and Devel. 1:268-76); the alpha-feto-protein gene control region in liver (Krumlauf et al., 1985, Mol. Cell. Biol., 5:1639-48; Hammer et al., 1987, Science 235:53-58); the alpha 1-antitrypsin gene control region in liver (Kelsey et al., 1987, Genes and Devel. 1:161-71); the beta-globin gene control region in myeloid cells (Mogram et al., 1985, Nature 315:338-40; Kollias et al., 1986, Cell 46:89-94); the myelin basic protein gene control region in oligodendrocyte cells in the brain (Readhead et al., 1987, Cell 48:703-12); the myosin light chain-2 gene control region in skeletal muscle (Sani, 1985, Nature 314:283-86); the gonadotropic releasing hormone gene control region in the hypothalamus (Mason et al., 1986, Science 234:1372-78), and the tyrosinase promoter in melanoma cells (Hart, I. Semin Oncol 1996 February; 23(1):154-8; Siders, et al. Cancer Gene Ther 1998 September-October; 5(5):281-91), among others. Inducible promoters that are activated in the presence of a certain molecule or condition such as light, heat, radiation, tetracycline, or heat shock proteins, for example, may also be utilized (see, for example, WO 00/10612). Other suitable promoters are known in the art.

As described above, enhancers may also be suitable flanking sequences. Enhancers are cis-acting elements of DNA, usually about 10-300 bp in length, that act on the promoter to increase transcription. Enhancers are typically orientation- and position-independent, having been identified both 5' and 3' to controlled coding sequences. Several enhancer sequences available from mammalian genes are known (i.e., globin, elastase, albumin, alpha-feto-protein and insulin). Similarly, the SV40 enhancer, the cytomegalovirus early promoter enhancer, the polyoma enhancer, and adenovirus enhancers are useful with eukaryotic promoter sequences. While an enhancer may be spliced into the vector at a position 5' or 3' to nucleic acid coding sequence, it is typically located at a site 5' from the promoter. Other suitable enhancers are known in the art, and would be applicable to the present invention.

In certain embodiments, it may be advantageous to combine a p62 polypeptide or nucleic acid sequence encoding a p62 polypeptide, or derivative thereof with one or more co-stimulatory component(s) such as cell surface proteins, cytokines, chemokines, or signaling molecules in a composition of the present invention. The co-stimulatory component may be included in the composition as a polypeptide or as a nucleic acid encoding the polypeptide, for example.

Suitable co-stimulatory molecules include, for instance, polypeptides that bind members of the CD28 family (i.e., CD28, ICOS; Hutloff, et al. Nature 1999, 397: 263-265; Peach, et al. J Exp Med 1994, 180: 2049-2058) such as the CD28 binding polypeptides B7.1 (CD80; Schwartz, 1992; Chen et al, 1992; Ellis, et al. J. Immunol., 156(8): 2700-9) and B7.2 (CD86; Ellis, et al. J. Immunol., 156(8): 2700-9); polypeptides which bind members of the integrin family (i.e., LFA-1 (CD11a/CD18); Sedwick, et al. J Immunol 1999, 162: 1367-1375; Wulfing, et al. Science 1998, 282: 2266-2269; Lub, et al. Immunol Today 1995, 16: 479-483) including members of the ICAM family (i.e., ICAM-1, -2 or -3); polypeptides which bind CD2 family members (i.e., CD2, signalling lymphocyte activation molecule (CDw150 or "SLAM"; Aversa, et al. J Immunol 1997, 158: 4036-4044)) such as CD58 (LFA-3; CD2 ligand; Davis, et al. Immunol Today 1996, 17: 177-187) or SLAM ligands (Sayos, et al. Nature 1998, 395: 462-469); polypeptides which bind heat stable antigen (HSA or CD24; Zhou, et al. Eur J Immunol 1997, 27: 2524-2528); polypeptides which bind to members of the TNF receptor (TNFR) family (i.e., 4-1BB (CD137; Vinay, et al. Semin Immunol 1998, 10: 481-489), OX40 (CD134; Weinberg, et al. Semin Immunol 1998, 10: 471-480; Higgins, et al J Immunol 1999, 162: 486-493), and CD27 (Lens, et al. Semin Immunol 1998, 10: 491-499)) such as 4-1BBL (4-1BB ligand; Vinay, et al. Semin Immunol 1998, 10: 481-48; DeBenedette, et al. J Immunol 1997, 158: 551-559), TNFR associated factor-1 (TRAF-1; 4-1BB ligand; Saoulli, et al. J Exp Med 1998, 187: 1849-1862, Arch, et al. Mol Cell Biol 1998, 18: 558-565), TRAF-2 (4-1BB and OX40 ligand; Saoulli, et al. J Exp Med 1998, 187: 1849-1862; Oshima, et al. Int Immunol 1998, 10: 517-526, Kawamata, et al. J Biol Chem 1998, 273: 5808-5814), TRAF-3 (4-1BB and OX40 ligand; Arch, et al. Mol Cell Biol 1998, 18: 558-565; Jang, et al. Biochem Biophys Res Commun 1998, 242: 613-620; Kawamata S, et al. J Biol Chem 1998, 273: 5808-5814), OX4OL (OX40 ligand; Gramaglia, et al. J Immunol 1998, 161: 6510-6517), TRAF-5 (OX40 ligand; Arch, et al. Mol Cell Biol 1998, 18: 558-565; Kawamata, et al. J Biol Chem 1998, 273: 5808-5814), and CD70 (CD27, ligand; Couderc, et al. Cancer Gene Ther., 5(3): 163-75). CD154 (CD40 ligand or "CD4OL"; Gurunathan, et al. J. Immunol., 1998, 161: 4563-4571; Sine, et al. Hum. Gene Ther., 2001, 12: 1091-1102) may also be suitable.

One or more cytokines may also be suitable co-stimulatory components or "adjuvants", either as polypeptides or being encoded by nucleic acids contained within the compositions of the present invention (Parmiani, et al. Immunol Left 2000 Sep. 15; 74(1): 41-4; Berzofsky, et al. Nature Immunol 1: 209-219). Suitable cytokines include, for example, interleukin-2 (IL-2) (Rosenberg, et al. Nature Med. 4: 321-327 (1998)), IL-4, IL-7, IL-12 (reviewed by Pardoll, 1992; Harries, et al. J. Gene Med. 2000 July-August; 2(4): 243-9; Rao, et al. J. Immunol. 156: 3357-3365 (1996)), IL-15 (Xin, et al. Vaccine, 17:858-866, 1999), IL-16 (Cruikshank, et al. J. Leuk Biol. 67(6): 757-66, 2000), IL-18 (J. Cancer Res. Clin. Oncol. 2001. 127(12): 718-726), GM-CSF (CSF (Disis, et al. Blood, 88: 202-210 (1996)), tumor necrosis factor-alpha (TNF-.alpha.), or interferons such as IFN-.alpha. or INF-.gamma. Other cytokines may also be suitable for practicing the present invention, as is known in the art.

Chemokines may also be utilized. For example, fusion proteins comprising CXCL10 (IP-10) and CCL7 (MCP-3) fused to a tumor self-antigen have been shown to induce anti-tumor immunity (Biragyn, et al. Nature Biotech. 1999, 17: 253-258). The chemokines CCL3 (MIP-1.alpha.) and CCL5 (RANTES) (Boyer, et al. Vaccine, 1999, 17 (Supp. 2): S53-S64) may also be of use in practicing the present invention. Other suitable chemokines are known in the art.

A "signaling molecule" is a chemical biological compound involved in transmitting information between cells. Such molecules are released from the cell sending the signal, cross over the gap between cells by diffusion, and interact with specific receptors in another cell, triggering a response in that cell by activating a series of enzyme controlled reactions which lead to changes inside the cell. For example, hydrogen sulfide is produced in small amounts by some cells of the human body and has a number of biological signaling functions. Only examples include nitric oxide and carbon monoxide.

It is also known in the art that suppressive or negative regulatory immune mechanisms may be blocked, resulting in enhanced immune responses. For instance, treatment with anti-CTLA-4 antibody (Shrikant, et al. Immunity, 1996, 14: 145-155; Sutmuller, et al. J. Exp. Med., 2001, 194: 823-832), anti-CD25 antibody (Sutmuller, supra), anti-CD4 antibody (Matsui, et al. J. Immunol., 1999, 163: 184-193), the fusion protein IL13Ra2-Fc (Terabe, et al. Nature Immunol., 2000, 1: 515-520), and combinations thereof (i.e., anti-CTLA-4 and anti-CD25 antibodies, Sutmuller, supra) have been shown to upregulate anti-tumor immune responses and would be suitable in practicing the present invention.

Any of these components may be used alone or in combination with other agents. For instance, it has been shown that a combination of CD80, ICAM-1 and LFA-3 ("TRICOM") may potentiate anti-cancer immune responses (Hodge, et al. Cancer Res. 59: 5800-5807 (1999). Other effective combinations include, for example, IL-12+GM-CSF (Ahlers, et al. J. Immunol., 158: 3947-3958 (1997); Iwasaki, et al. J. Immunol 158: 4591-4601 (1997)), IL-12+GM-CSF+TNF-α. (Ahlers, et al. Int. Immunol 13: 897-908 (2001)), CD80+IL-12 (Fruend, et al. Int. J. Cancer, 85: 508-517 (2000); Rao, et al. supra), and CD86+GM-CSF+IL-12 (Iwasaki, supra). One of skill in the art would be aware of additional combinations useful in carrying out the present invention. In addition, the skilled artisan would be aware of additional reagents or methods that may be used to modulate such mechanisms. These reagents and methods, as well as others known by those of skill in the art, may be utilized in practicing the present invention.

Additional strategies for improving the efficiency of nucleic acid-based immunization may also be used including, for example, the use of self-replicating viral replicons (Caley, et al. 1999. Vaccine, 17: 3124-2135; Dubensky, et al. 2000. Mol. Med. 6: 723-732; Leitner, et al. 2000. Cancer Res. 60: 51-55), codon optimization (Liu, et al. 2000. Mol. Ther., 1: 497-500; Dubensky, supra; Huang, et al. 2001. J. Virol. 75: 4947-4951), in vivo electroporation (Widera, et al. 2000. J. Immunol. 164: 4635-3640), incorporation of CpG stimulatory motifs (Gurunathan, et al. Ann. Rev. Immunol., 2000, 18: 927-974; Leitner, supra; Cho, et al. J. Immunol 168(10):4907-13), sequences for targeting of the endocytic or ubiquitin-processing pathways (Thomson, et al. 1998. J. Virol. 72: 2246-2252; Velders, et al. 2001. J. Immunol 166: 5366-5373), Marek's disease virus type 1 VP22 sequences (J. Virol. 76(6):2676-82, 2002), prime-boost regimens (Gurunathan, supra; Sullivan, et al. 2000. Nature, 408: 605-609; Hanke, et al. 1998. Vaccine, 16: 439-445; Amara, et al. 2001. Science, 292: 69-74), and the use of mucosal delivery vectors such as *Salmonella* (Darji, et al. 1997. Cell, 91:

765-775; Woo, et al. 2001. Vaccine, 19: 2945-2954). Other methods are known in the art, some of which are described below.

Chemotherapeutic agents, radiation, anti-angiogenic molecules, or other agents may also be utilized in treating and/or preventing cancer using p62 polypeptides or p62-encoding nucleic acids (Sebti, et al. Oncogene 2000 Dec. 27; 19(56): 6566-73). For example, in treating metastatic breast cancer, useful chemotherapeutic agents include cyclophosphamide, doxorubicin, paclitaxel, docetaxel, navelbine, capecitabine, and mitomycin C, among others. Combination chemotherapeutic regimens have also proven effective including cyclophosphamide+methotrexate+5-fluorouracil; cyclophosphamide+doxorubicin+5-fluorouracil; or, cyclophosphamide+doxorubicin, for example. Other compounds such as prednisone, a taxane, navelbine, mitomycin C, or vinblastine have been utilized for various reasons. A majority of breast cancer patients have estrogen-receptor positive (ER+) tumors and in these patients, endocrine therapy (i.e., tamoxifen) is preferred over chemotherapy. For such patients, tamoxifen or, as a second line therapy, progestins (medroxyprogesterone acetate or megestrol acetate) are preferred. Aromatase inhibitors (i e, aminoglutethimide and analogs thereof such as letrozole) decrease the availability of estrogen needed to maintain tumor growth and may be used as second or third line endocrine therapy in certain patients.

Other cancers may require different chemotherapeutic regimens. For example, metastatic colorectal cancer is typically treated with Camptosar (irinotecan or CPT-11), 5-fluorouracil or leucovorin, alone or in combination with one another. Proteinase and integrin inhibitors such as the MMP inhibitors marimastate (British Biotech), COL-3 (Collagenex), Neovastat (Aeterna), AG3340 (Agouron), BMS-275291 (Bristol Myers Squibb), CGS 27023A (Novartis) or the integrin inhibitors Vitaxin (Medimmune), or MED 1522 (Merck KgaA) may also be suitable for use. As such, immunological targeting of immunogenic targets associated with colorectal cancer could be performed in combination with a treatment using those chemotherapeutic agents. Similarly, chemotherapeutic agents used to treat other types of cancers are well-known in the art and may be combined with the immunogenic targets described herein.

Many anti-angiogenic agents are known in the art and would be suitable for co-administration with the p62 nucleic acid or polypeptide vaccines (see, for example, Timar, et al. 2001. Pathology Oncol. Res., 7(2): 85-94). Such agents include, for example, physiological agents such as growth factors (i.e., ANG-2, NK1, 2, 4 (HGF), transforming growth factor beta (TGF-$\beta$)), cytokines (i.e., interferons such as IFN-$\alpha$, -$\beta$, -$\gamma$, platelet factor 4 (PF-4), PR-39), proteases (i.e., cleaved AT-III, collagen XVIII fragment (Endostatin)), HmwKallikrein-d5 plasmin fragment (Angiostatin), prothrombin-F1-2, TSP-1), protease inhibitors (i.e., tissue inhibitor of metalloproteases such as TIMP-1, -2, or -3; maspin; plasminogen activator-inhibitors such as PAI-1; pigment epithelium derived factor (PEDF)), Tumstatin (available through ILEX, Inc.), antibody products (i.e., the collagen-binding antibodies HUIV26, HUI77, XL313; anti-VEGF; anti-integrin (i.e., Vitaxin, (Lxsys))), and glycosidases (i.e., heparinase-I, -III). Molecules that are antagonists to angiogenesis-associated antigens (including proteins and polypeptides) are also suitable and can include, but are not limited to, molecules directed against VEGF, VEGF receptor, EGFR, bFGF, PDGF-B, PD-ECGF, TGFs including TGF-$\alpha$, endoglin, Id proteins, various proteases, nitric oxide synthase, aminopeptidase, thrombospondins, k-ras, Wnt, cyclin-dependent kinases, microtubules, heat shock proteins, heparin-binding factors, synthases, collagen receptors, integrins, and surface proteoglycan NG2. "Chemical" or modified physiological agents known or believed to have anti-angiogenic potential include, for example, vinblastine, taxol, ketoconazole, thalidomide, dolestatin, combrestatin A, rapamycin (Guba, et al. 2002, Nature Med., 8: 128-135), CEP-7055 (available from Cephalon, Inc.), flavone acetic acid, Bay 12-9566 (Bayer Corp.), AG3340 (Agouron, Inc.), CGS. 27023A (Novartis), tetracylcine derivatives (i.e., COL-3 (Collagenix, Inc.)), Neovastat (Aeterna), BMS-275291 (Bristol-Myers Squibb), low dose 5-FU, low dose methotrexate (MTX), irsofladine, radicicol, cyclosporine, captopril, celecoxib, D45152-sulphated polysaccharide, cationic protein (Protamine), cationic peptide-VEGF, Suramin (polysulphonated napthyl urea), compounds that interfere with the function or production of VEGF (i.e., SU5416 or SU6668 (Sugen), PTK787/ZK22584 (Novartis)), Distamycin A, Angiozyme (ribozyme), isoflavinoids, staurosporine derivatives, genistein, EMD121974 (Merck KcgaA), tyrphostins, isoquinolones, retinoic acid, carboxyamidotriazole, TNP-470, octreotide, 2-methoxyestradiol, aminosterols (i.e., squalamine), glutathione analogues (i.e., N-acteyl-L-cysteine), combretastatin A-4 (Oxigene), Eph receptor blocking agents (Nature, 414:933-938, 2001), Rh-Angiostatin, Rh-Endostatin (WO 01/93897), cyclic-RGD peptide, accutin-disintegrin, benzodiazepenes, humanized anti-avb3 Ab, Rh-PAI-2, amiloride, p-amidobenzamidine, anti-uPA ab, anti-uPAR Ab, L-phenylalanine-N-methylamides (i.e., Batimistat, Marimastat), AG3340, and minocycline. Many other suitable agents are known in the art and would suffice in practicing the present invention.

The present invention may also be utilized in combination with "non-traditional" methods of treating cancer. For example, it has been demonstrated that administration of certain anaerobic bacteria may assist in slowing tumor growth. In one study, *Clostridium novyi* was modified to eliminate a toxin gene carried on a phage episome and administered to mice with colorectal tumors (Dang, et al. P.N.A.S. USA, 98(26): 15155-15160, 2001). In combination with chemotherapy, the treatment was shown to cause tumor necrosis in the animals. The reagents and methodologies described in this application may be combined with such treatment methodologies.

Nucleic acids encoding p62 polypeptides may be administered to patients by any of several available techniques. Various viral vectors that have been successfully utilized for introducing a nucleic acid to a host include retrovirus, adenovirus, adeno-associated virus (AAV), herpes virus, and poxvirus, among others. It is understood in the art that many such viral vectors are available in the art. The vectors of the present invention may be constructed using standard recombinant techniques widely available to one skilled in the art. Such techniques may be found in common molecular biology references such as Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), and PCR Protocols: A Guide to Methods and Applications (Innis, et al. 1990. Academic Press, San Diego, Calif.).

Suitable retroviral vectors include derivatives of lentivirus as well as derivatives of murine or avian retroviruses. Examples of suitable retroviral vectors include, for example, Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of retroviral vectors can incorporate multiple exogenous nucleic acid sequences. As recombinant retroviruses are defective, they require assistance in order to produce infectious vector particles. This assistance can be provided by, for example, helper cell lines encoding retrovirus structural genes. Suitable helper cell lines include .PSI.2, PA317 and PA12, among others. The vector virions produced using such cell lines may then be used to infect a tissue cell line, such as NIH 3T3 cells, to produce large quantities of chimeric retroviral virions. Retroviral vectors may be administered by traditional methods (i.e., injection) or by implantation of a "producer cell line" in proximity to the target cell population (Culver, K., et al., 1994, Hum. Gene Ther., 5 (3): 343-79; Culver, K., et al., Cold Spring Harb. Symp; Quant. Biol., 59: 685-90); Oldfield, E., 1993, Hum. Gene Ther., 4 (1): 39-69). The producer cell line is engineered to produce a viral vector and releases viral particles in the vicinity of the target cell. A portion of the released viral particles contact the target cells and infect those cells, thus delivering a nucleic acid of the present invention to the target cell. Following infection of the target cell, expression of the nucleic acid of the vector occurs.

Adenoviral vectors have proven especially useful for gene transfer into eukaryotic cells (Rosenfeld, M., et al., 1991, Science, 252 (5004): 431-4; Crystal, R., et al., 1994, Nat. Genet., 8 (1): 42-51), the study eukaryotic gene expression (Levrero, M., et al., 1991, Gene, 101 (2): 195-202), vaccine development (Graham, F. and Prevec, L., 1992, Biotechnology, 20: 363-90), and in animal models (Stratford-Perricaudet, L., et al., 1992, Bone Marrow Transplant., 9 (Suppl. 1): 151-2; Rich, D., et al., 1993, Hum. Gene Ther., 4 (4): 461-76). Experimental routes for administrating recombinant adenovirus to different tissues in vivo have included intratracheal instillation (Rosenfeld, M., et al., 1992, Cell, 68 (1): 143-55) injection into muscle (Quantin, B., et al., 1992, Proc. Natl. Acad. Sci. U.S.A., 89 (7): 2581-4), peripheral intravenous injection (Herz, J., and Gerard, R., 1993, Proc. Natl. Acad. Sci. U.S.A., 90 (7): 2812-6) and stereotactic inoculation to brain (Le Gal La Salle, G., et al., 1993, Science, 259 (5097): 988-90), among others.

Adeno-associated virus (AAV) demonstrates high-level infectivity, broad host range and specificity in integrating into the host cell genome (Hermonat, P., et al., 1984, Proc. Natl. Acad. Sci. U.S.A., 81 (20): 6466-70). And Herpes Simplex Virus type-1 (HSV-1) is yet another attractive vector system, especially for use in the nervous system because of its neurotropic property (Geller, A., et al., 1991, Trends Neurosci., 14 (10): 428-32; Glorioso, et al., 1995, Mol. Biotechnol., 4 (1): 87-99; Glorioso et al., 1995, Annu. Rev. Microbiol., 49: 675-710).

Poxvirus is another useful expression vector (Smith, et al. 1983, Gene, 25 (1): 21-8; Moss, et al, 1992, Biotechnology, 20: 345-62; Moss, et al, 1992, Curr. Top. Microbiol. Immunol., 158: 25-38; Moss, et al. 1991. Science, 252: 1662-1667). Poxviruses shown to be useful include vaccinia, NYVAC, avipox, fowlpox, canarypox, ALVAC, and ALVAC (2), among others.

NYVAC (vP866) was derived from the Copenhagen vaccine strain of vaccinia virus by deleting six nonessential regions of the genome encoding known or potential virulence factors (see, for example, U.S. Pat. Nos. 5,364,773 and 5,494,807). The deletion loci were also engineered as recipient loci for the insertion of foreign genes. The deleted regions are: thymidine kinase gene (TK; J2R); hemorrhagic region (u; B13R+B14R); A type inclusion body region (ATI; A26L); hemagglutinin gene (HA; A56R); host range gene region (C7L-K1L); and, large subunit, ribonucleotide reductase (I4L). NYVAC is a genetically engineered vaccinia virus strain that was generated by the specific deletion of eighteen open reading frames encoding gene products associated with virulence and host range. NYVAC has been show to be useful for expressing TAs (see, for example, U.S. Pat. No. 6,265,189). NYVAC (vP866), vP994, vCP205, vCP1433, placZH6H4Lreverse, pMPC6H6K3E3 and pC3H6FHVB were also deposited with the ATCC under the terms of the Budapest Treaty, accession numbers VR-2559, VR-2558, VR-2557, VR-2556, ATCC-97913, ATCC-97912, and ATCC-97914, respectively.

ALVAC-based recombinant viruses (i.e., ALVAC-1 and ALVAC-2) are also suitable for use in practicing the present invention (see, for example, U.S. Pat. No. 5,756,103). ALVAC(2) is identical to ALVAC(1) except that ALVAC(2) genome comprises the vaccinia E3L and K3L genes under the control of vaccinia promoters (U.S. Pat. No. 6,130,066; Beattie et al., 1995a, 1995b, 1991; Chang et al., 1992; Davies et al., 1993). Both ALVAC(1) and ALVAC(2) have been demonstrated to be useful in expressing foreign DNA sequences, such as TAs (Tartaglia et al., 1993 a,b; U.S. Pat. No. 5,833,975). ALVAC was deposited under the terms of the Budapest Treaty with the American Type Culture Collection (ATCC), 10801 University Boulevard, Manassas, Va. 20110-2209, USA, ATCC accession number VR-2547.

Another useful poxvirus vector is TROVAC. TROVAC refers to an attenuated fowlpox that was a plaque-cloned isolate derived from the FP-1 vaccine strain of fowlpoxvirus which is licensed for vaccination of 1 day old chicks. TROVAC was likewise deposited under the terms of the Budapest Treaty with the ATCC, accession number 2553.

"Non-viral" plasmid vectors may also be suitable in practicing the present invention. Suitable plasmid vectors are compatible with bacterial, insect, and/or mammalian host cells. Such vectors include, for example, PCR-II, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT pub. No. WO 90/14363) and pFastBacDual (Gibco-BRL, Grand Island, N.Y.) as well as Bluescript® plasmid derivatives (a high copy number COLE1-based phagemid, Stratagene Cloning Systems, La Jolla, Calif.), PCR cloning plasmids designed for cloning Taq-amplified PCR products (e.g., TOPO™ TA Cloning® kit, PCR2.1® plasmid derivatives, Invitrogen, Carlsbad, Calif.). Bacterial vectors may also be used with the current invention. These vectors include, for example, *Shigella, Salmonella, Vibrio cholerae, Lactobacillus, Bacille calmette guerin* (BCG), and *Streptococcus* (see for example, WO 88/6626; WO 90/0594; WO 91/13157; WO 92/1796; and WO 92/21376). Many other non-viral plasmid expression vectors and systems are known in the art and could be used with the current invention.

Suitable nucleic acid delivery techniques include DNA-ligand complexes, adenovirus-ligand-DNA complexes, direct injection of DNA, $CaPO_4$ precipitation, gene gun techniques, electroporation, and colloidal dispersion systems, among others. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome, which are artificial membrane vesicles useful as delivery vehicles in vitro and in vivo. RNA, DNA and intact virions can be encapsulated within the aqueous interior and be delivered to cells in a biologically active form (Fraley, R., et al., 1981, Trends Biochem. Sci., 6: 77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

An immunogenic target may also be administered in combination with one or more adjuvants to boost the immune response. Exemplary adjuvants are shown in Table 3 below:

TABLE 3

Types of Immunologic Adjuvants

| Type of Adjuvant | General Examples | Specific Examples/References |
| --- | --- | --- |
| Gel-type | Aluminum hydroxide/phosphate ("alum adjuvants") | (Aggerbeck and Heron, 1995) |
|  | Calcium phosphate | (Relyveld, 1986) |
| Microbial | Muramyl dipeptide (MDP) | (Chedid et al., 1986) |
|  | Bacterial exotoxins | Cholera toxin (CT), *E. coli* labile toxin (LT) (Freytag and Clements, 1999) |
|  | Endotoxin-based adjuvants | Monophosphoryl lipid A (MPL) (Ulrich and Myers, 1995) |
|  | Other bacterial | CpG oligonucleotides (Corral and Petray, 2000), BCG sequences (Krieg, et al. Nature, 374: 576), tetanus toxoid (Rice, et al. J. Immunol., 2001, 167: 1558-1565) |
| Particulate | Biodegradable Polymer microspheres | (Gupta et al., 1998) |
|  | Immunostimulatory complexes (ISCOMs) | (Morein and Bengtsson, 1999) |
|  | Liposomes | (Wassef et al., 1994) |
| Oil-emulsion and surfactant-based adjuvants | Freund's incomplete adjuvant | (Jensen et al., 1998) |
|  | Microfluidized emulsions | MF59 (Ott et al., 1995) SAF (Allison and Byars, 1992) (Allison, 1999) |
|  | Saponins | QS-21 (Kensil, 1996) |
| Synthetic | Muramyl peptide derivatives | Murabutide (Lederer, 1986), Threony-MDP (Allison, 1997) |
|  | Nonionic block copolymers | L121 (Allison, 1999) |
|  | Polyphosphazene (PCPP) | (Payne et al., 1995) |
|  | Synthetic polynucleotides | Poly A: U, Poly I: C (Johnson, 1994) |
|  | Thalidomide derivatives | CC-4047/ACTIMID (J. Immunol., 168(10): 4914-9) |

In some embodiments, p62 polypeptides or p62 encoding nucleic acids in accordance with the present invention may be used to treat, alleviate, ameliorate, relieve, delay onset of (prophylaxis), inhibit progression of, reduce severity of, and/or reduce incidence of one or more symptoms or features of a disease, disorder, and/or condition. In some embodiments, p62 polypeptides or p62 encoding nucleic acids can be used to treat solid tumors, e.g., cancer and/or cancer cells. The term "cancer" includes pre-malignant as well as malignant cancers. Cancers include, but are not limited to, prostate cancer, gastric cancer, colorectal cancer, skin cancer, e.g., melanomas or basal cell carcinomas, lung cancer, breast cancer, ovarian cancer, uterine cancer, cancers of the head and neck, bronchus cancer, pancreatic cancer, urinary bladder cancer, brain or central nervous system cancer, peripheral nervous system cancer, esophageal cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, sarcoma, cancer of hematological tissues, and the like. "Cancer cells" can be in the form of a tumor, exist alone within a subject (e.g., leukemia cells or ascites), or be cell lines derived from a cancer.

Cancer can be associated with a variety of physical symptoms. Symptoms of cancer generally depend on the type and location of the tumor. For example, lung cancer can cause coughing, shortness of breath, and chest pain, while colon cancer often causes diarrhea, constipation, and blood in the stool. However, to give but a few examples, the following symptoms are often generally associated with many cancers: fever, chills, night sweats, cough, dyspnea, weight loss, loss of appetite, anorexia, nausea, vomiting, diarrhea, anemia, jaundice, hepatomegaly, hemoptysis, fatigue, malaise, cognitive dysfunction, depression, hormonal disturbances, neutropenia, pain, non-healing sores, enlarged lymph nodes, peripheral neuropathy, and sexual dysfunction.

In one aspect of the invention, a method for the treatment of cancer (e.g. prostate or breast cancer) is provided. In some embodiments, the treatment of cancer comprises administering a therapeutically effective amount of p62 polypeptides or p62 encoding nucleic acids to a subject in need thereof, in such amounts and for such time as is necessary to achieve the desired result. In certain embodiments of the present invention a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

In one aspect of the invention, a method for administering p62 polypeptides or p62 encoding nucleic acids to a subject suffering from cancer (e.g. breast cancer) or relapse is provided. In some embodiments, p62 polypeptides or p62 encoding nucleic acids are administered to a subject in such amounts and for such time as is necessary to achieve the desired result (i.e. treatment of cancer). In certain embodiments of the present invention a "therapeutically effective amount" of p62 polypeptides and p62 encoding nucleic acids is that amount effective for treating, alleviating, ameliorating, relieving, delaying onset of, inhibiting progression of, reducing severity of, and/or reducing incidence of one or more symptoms or features of cancer. In some embodiments, the p62 polypeptides or p62 encoding nucleic acids of the invention are administered to a subject previously treated for cancer. In some embodiments, the p62 polypeptides or p62 encoding nucleic acids of the invention are administered to a subject with a family history of cancer. In some embodiments, the p62 polypeptides or p62 encoding nucleic acids of the invention are administered to a subject with a predisposition for cancer. For example, a subject who is BRCA-positive is genetically predisposed to certain forms of breast cancer.

Inventive therapeutic protocols include administering a therapeutically effective amount of p62 polypeptides or p62 encoding nucleic acids to a healthy individual (i.e., a subject who does not display any symptoms of cancer and/or who has not been diagnosed with cancer). For example, healthy individuals may be "immunized" with p62 polypeptides or p62 encoding nucleic acids prior to development of cancer and/or onset of symptoms of cancer; at risk individuals (e.g., patients who have a family history of cancer; patients carrying one or more genetic mutations associated with development of cancer; patients having a genetic polymorphism associated with development of cancer; patients infected by a virus associated with development of cancer; patients with habits and/or lifestyles associated with development of cancer; etc.) can be treated substantially contemporaneously with (e.g., within 48 hours, within 24 hours, or within 12 hours of) the onset of symptoms of cancer. Of course individuals known to have cancer may receive inventive treatment at any time.

In other embodiments, the p62 polypeptides or p62 encoding nucleic acids of the present invention can be used to inhibit the growth of cancer cells, e.g., breast cancer cells. As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth Inhibition of cancer growth is also generally correlated with prolonged survival and/or increased health and well-being of the subject.

Compounds and compositions described herein can be administered as a pharmaceutical or medicament formulated with a pharmaceutically acceptable carrier. Accordingly, the compounds and compositions may be used in the manufacture of a medicament or pharmaceutical composition. Pharmaceutical compositions of the invention may be formulated as solutions or lyophilized powders for parenteral administration. Powders may be reconstituted by addition of a suitable diluent or other pharmaceutically acceptable carrier prior to use. Liquid formulations may be buffered, isotonic, aqueous solutions. Powders also may be sprayed in dry form. Examples of suitable diluents are normal isotonic saline solution, standard 5% dextrose in water, or buffered sodium or ammonium acetate solution. Such formulations are especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride, sodium citrate, and the like.

Alternately, compounds and compositions may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation may be in the form of a syrup, elixir, emulsion, or an aqueous or non-aqueous suspension. For rectal administration, the invention compounds may be combined with excipients such as cocoa butter, glycerin, gelatin or polyethylene glycols and molded into a suppository.

Compounds and compositions may be formulated to include other medically useful drugs or biological agents. The compounds and compositions also may be administered in conjunction with the administration of other drugs or biological agents useful for the disease or condition to which the invention compounds and compositions are directed.

As employed herein, the phrase "an effective amount," refers to a dose sufficient to provide concentrations high enough to impart a beneficial effect on the recipient thereof. The specific therapeutically effective dose level for any particular subject will depend upon a variety of factors including the disorder being treated, the severity of the disorder, the activity of the specific compound or composition, the route of administration, the rate of clearance of the compound or composition, the duration of treatment, the drugs used in combination or coincident with the compound or composition, the age, body weight, sex, diet, and general health of the subject, and like factors well known in the medical arts and sciences. Various general considerations taken into account in determining the "therapeutically effective amount" are known to those of skill in the art and are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990. Dosage levels typically fall in the range of about 0.001 up to 100 mg/kg/day; with levels in the range of about 0.05 up to 10 mg/kg/day are generally applicable. A compound or composition can be administered parenterally, such as intravascularly, intravenously, intraarterially, intramuscularly, intraocularly, intradermally, subcutaneously, or the like. Administration can also be orally, nasally, rectally, transdermally, intravaginally or inhalationally via an aerosol. A compound or composition can be administered to the organ having the tumor (or the potential target of the tumor) or the tumor itself. The compound or composition may be administered as a bolus, or slowly infused, or be administered as an intradermal, subcutaneous, intramuscular, or intraperitoneal injection.

A therapeutically effective dose can be estimated initially from cell culture assays by determining a p62 expression level upon introduction of a nucleic acid encoding a p62 polypeptide. A dose can then be formulated in animal models to achieve a suitable immune response and/or protection from tumor growth. Such information can be used to more accurately determine useful initial doses in humans. The exact formulation, route of administration and dosage can be chosen by the individual physician in view of the patient's condition.

EXAMPLES

Example 1

Cell Lines and Vector Construction

A 233-VSGA1 breast tumor cell line, overexpressing activated rat HER/2 neu oncogene was derived from a mouse mammary carcinoma arising in FVB/neu NT transgenic mice. This cell line was maintained as described (Nanni P, Pupa S M, Nicoletti G et al. Int J Cancer 2000; 87:186). HeLa cells (ATCC # CCL-2.2™) were propagated in ATCC complete growth medium (ATCC MD-6108).

The extracellular domain of rat HER2/neu was amplified by PCR and cloned into pcDNA3.1 vector (Invitrogen) as described (F M Venanzi, A Barucca, K Havas, M Capitani, M Provinciali S Scotti, A Concetti. Vaccine 2010 (22); 3841-7.)

As a source of cDNA encoding p62, total RNA was extracted from HeLa cells. Full length cDNA encoding the longer isoform of p62 (Transcript Variant 1, GenBank reference No. NP_003891) was amplified by PCR (HotStar HiFidelity Polymerase Kit Qiagen) using the following primers: FW: 5-CCCGCTAGCATGGCGTCGCTCAC-CGTG-3 (SEQ ID NO: 3) and REV: 5'-CCCAAGCTTTCA-CAACGGCGGGGGATGCTTTG-3' (SEQ ID NO: 4). PCR products were purified and Nhe I-Hind III digested fragments cloned into pcDNA3.1

The sequences of the inserted p62 DNA were confirmed by sequencing (MGWBiotech/M-medical, Martinsried, Germany). It was observed that the encoded polypeptide differed from the wild type amino acid sequence by two substitution mutations: C145R and Q418R.

Example 2

Preventive Anti-tumor Effect of p62 Immunization in a Mouse Breast Cancer Model

FVB/N mice were split into three groups (15 mice per group) and immunized with either:
1. pcDNA.3.1 (empty plasmid vector, negative control);
2. pcDNA.3.1 with pHER2 (positive control); or,
3. pcDNA.3.1 with p62 (experiment).

FVB/N females were anesthetized and, after exposure of the femoral quadriceps, injected with 100 μg DNA (1 mg/mL) in saline using an insulin syringe. Mice were immunized two times (at 4 and at 2 weeks before tumor challenge). The mice were challenged intradermally with $3\times10^5$ 233-VSGA1 tumor cells/100 μl PBS buffer in the flank. In all cases, tumors were measured by determining two perpendicular diameters with a caliper three times a week. Mice were sacrificed when the tumor ulcerated or reached 1 cm in any diameter.

Figure 4:
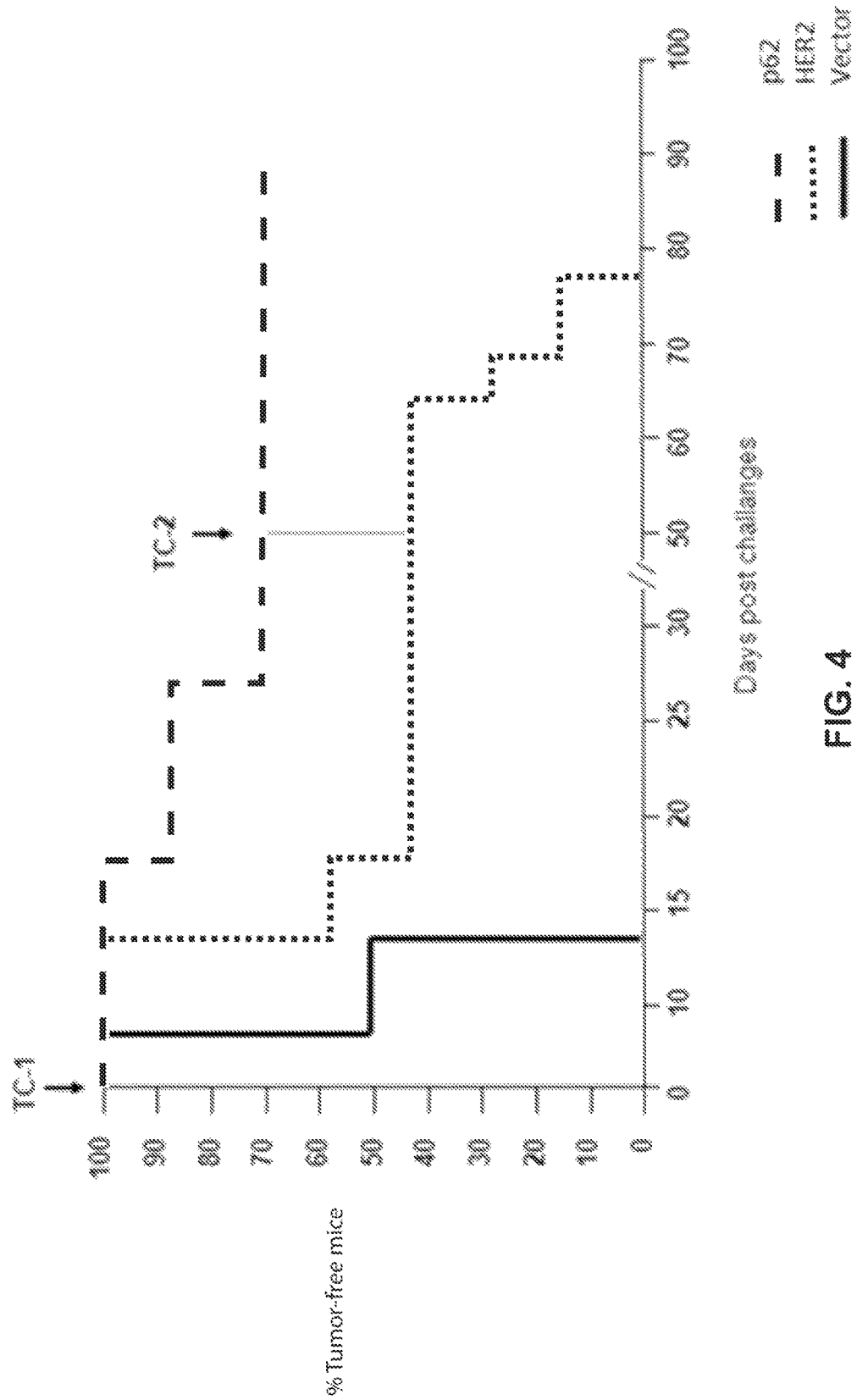
FIG. 4 shows a comparison of a time course of tumor formation in a mouse breast cancer model for mice injected with a DNA vaccine of either p62, HER2 (positive control), or vector alone (negative control).

100% of mice vaccinated with empty plasmid vector (negative control) have developed tumors by day 13 after challenge. Vaccination with HER2-encoding plasmid gave a 40% protection (FIG. 4). At the same time, p62-encoding plasmid demonstrated 100% protection by day 13, which gradually reduced to 70%. Consequently, the protective effect of p62-encoding plasmid in a transplantable breast cancer mouse model was demonstrated. Therefore, the preventive effect of the p62 vaccine was demonstrated for breast cancer in a mouse model. The inventors hypothesize that 100% protection could be maintained if vaccinations were continued.

Animals that were immunized with plasmid vector encoding either HER2 or p62 and did not develop tumors after the first cancer cells challenge were administered the same amount of cancer cells at day 50. All animals vaccinated with HER2-encoding plasmid developed tumors, while no tumors appeared in animals vaccinated with p62. Consequently, p62 immunization maintained immunological memory, whereas HER2 did not.

Example 3 p62 Vaccine Stimulates Innate Immunity

Figure 5:
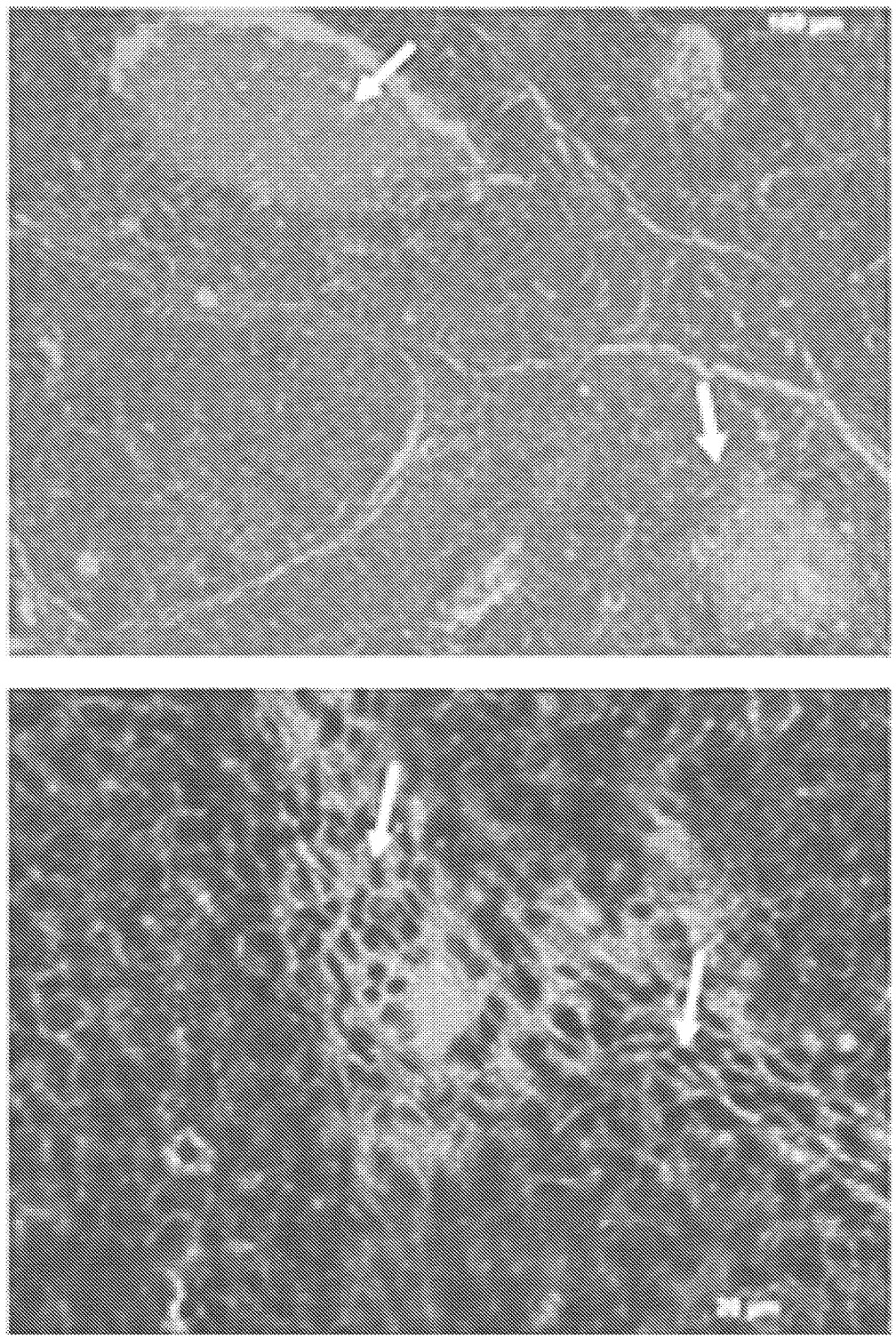
FIG. 5 shows Hematoxilin & Eosin (HE) staining of tumors from p62-immunized animals. The upper panel: arrows point to multiple foci of necrosis. The lower panel: arrows point to a meshwork of inflammatory cells.

The tumors in the mice receiving the p62 vaccine contained large zones of necrosis (FIG. 5). Immune cells associated with inflammation are abundantly present within the necrotic areas.

Figure 6:
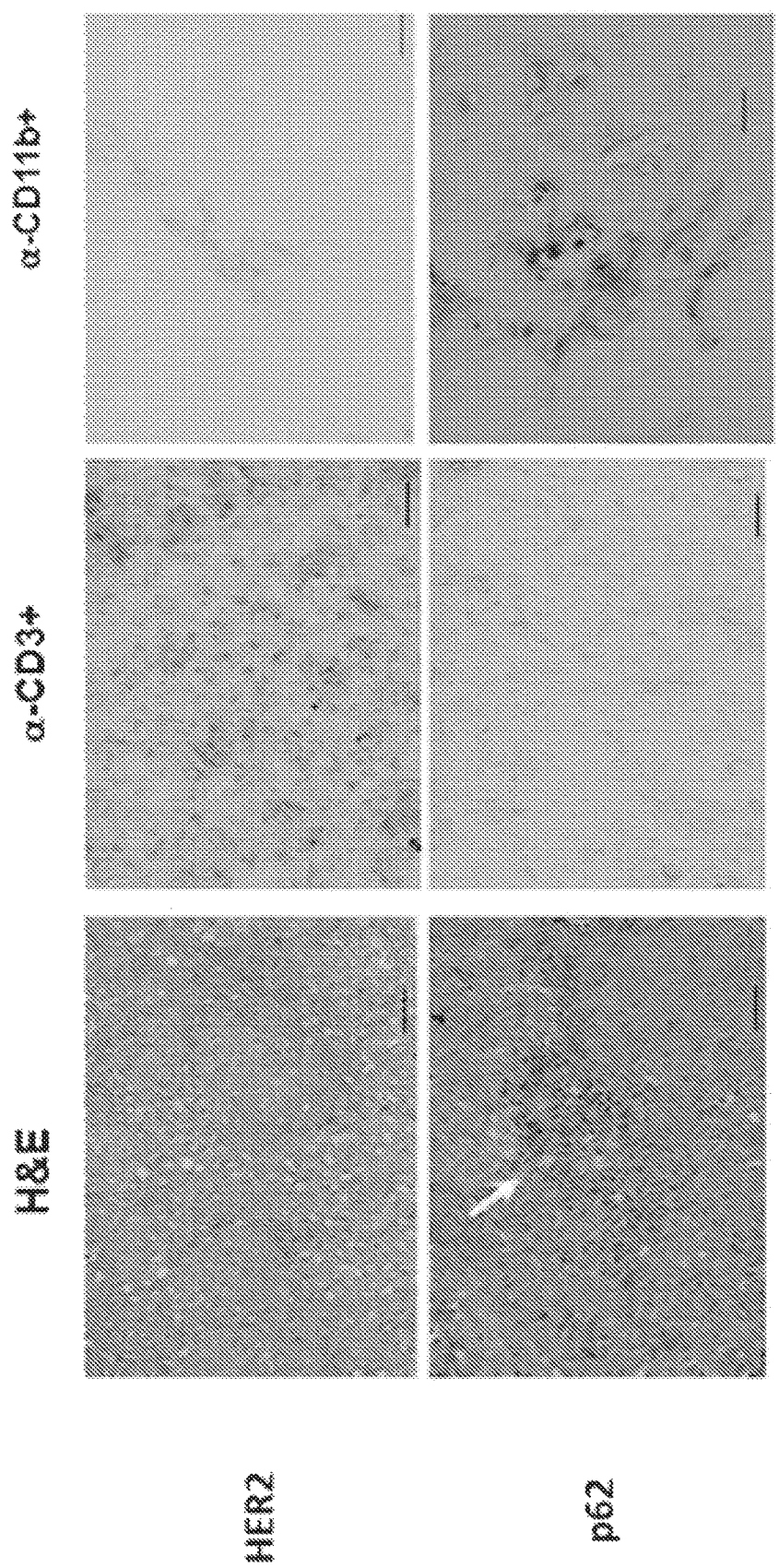
FIG. 6 shows immuno-histo-chemical staining of tumors from HER2- and p62-immunized animals. Left panels show HE staining, center panels show anti-CD3 staining, and right panels show anti-CD11b staining

The HER2 vaccine elicits antigen-specific adaptive immune response and massive migration of lymphocytes (CD3+ cells, tumor-infiltrating lymphocytes) into the tumor (FIG. 6). At the same time, vaccination with p62 plasmid did not significantly increase the level of tumor infiltrating lymphocytes. On the contrary, injection of p62 plasmid, but not the HER2 vaccine, increased the level of CD11B+ cells in the tumor (FIG. 6). Consequently, p62 vaccine acts through stimulation of innate immunity, unlike the HER2 vaccine.

Example 4

Figure 7:
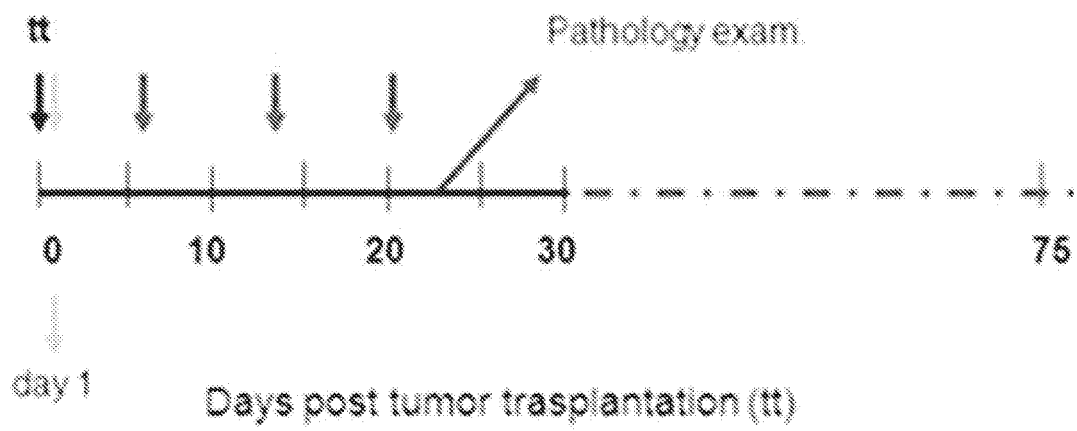
FIG. 7 shows a graphical timeline of p62 DNA vaccine administration in a T5 rat breast cancer model.

Demonstration of Anti-tumor Activity of p62 DNA Vaccine in T5 Rat Breast Cancer Model T5 transplantable rat breast cancer was derived from a spontaneous mammary gland adenocarcinoma of a Wistar rat in R.E. Kavetsky Institute of Experimental Pathology, Oncology and Radiobiology of National Academy of Sciences of Ukraine. Two month old female Wistar rats (weight—130-150 gm, 10 animals per group) were challenged with T5 rat mammary gland carcinoma by subcutaneous injection of $2.5 \times 10^6$ tumor cells/rat in 0.4 mL of PBS. Starting the next day after tumor transplantation, rats were vaccinated three times once a week (FIG. 7). Each injection contained 78 ug of pcDNA.3.1 (empty plasmid vector, negative control) or pcDNA.3.1 with p62 (experiment).

Figure 8:
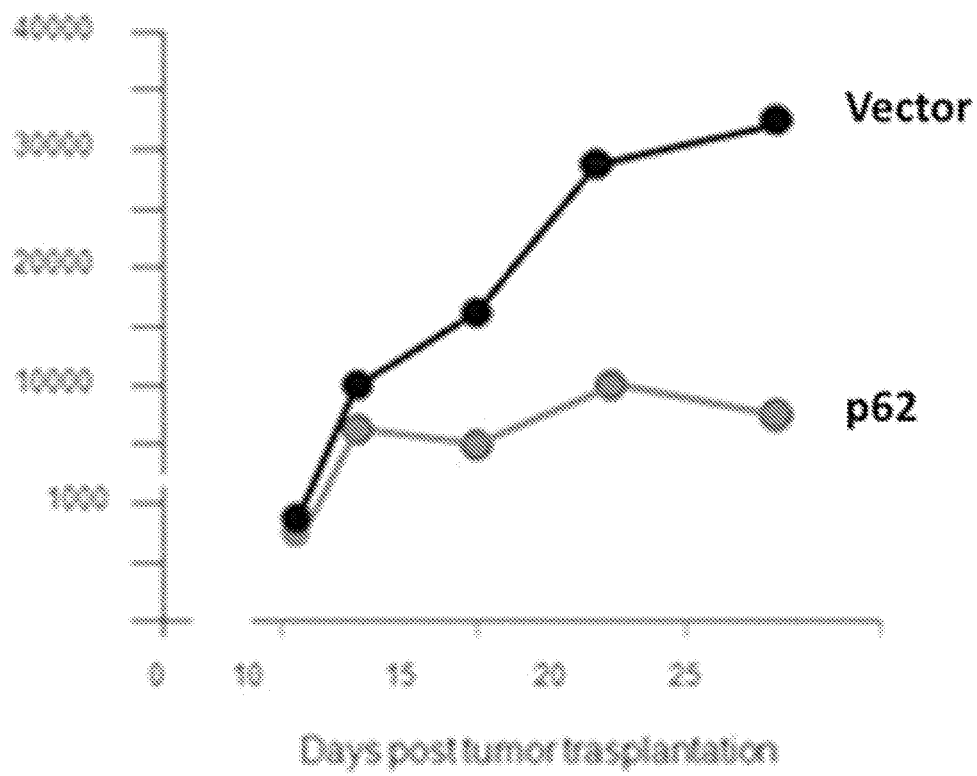
FIG. 8 shows a time course of tumor volume in p62-vaccinated and control rats with T5 transplantable breast carcinoma.
Figure 9:
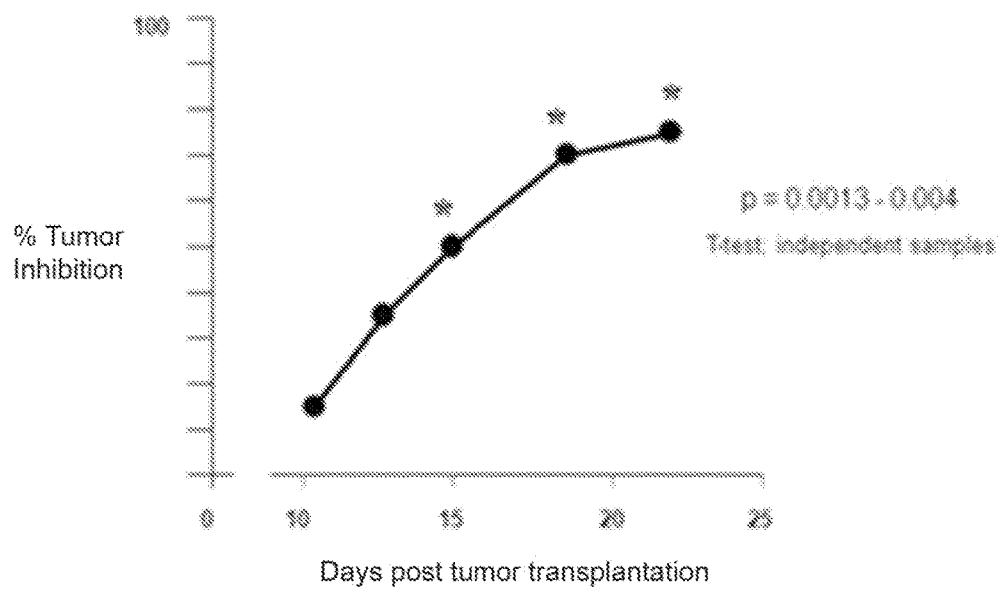
FIG. 9 shows a time course of tumor growth inhibition in p62-vaccinated and control rats with T5 transplantable breast carcinoma.

Tumor growth was inhibited by p62 immunization (FIG. 8) with a 70% tumor growth inhibition in p62-vaccinated rats compared to vector-injected control rats ($p<0.004$) (FIG. 9).

Figure 10:
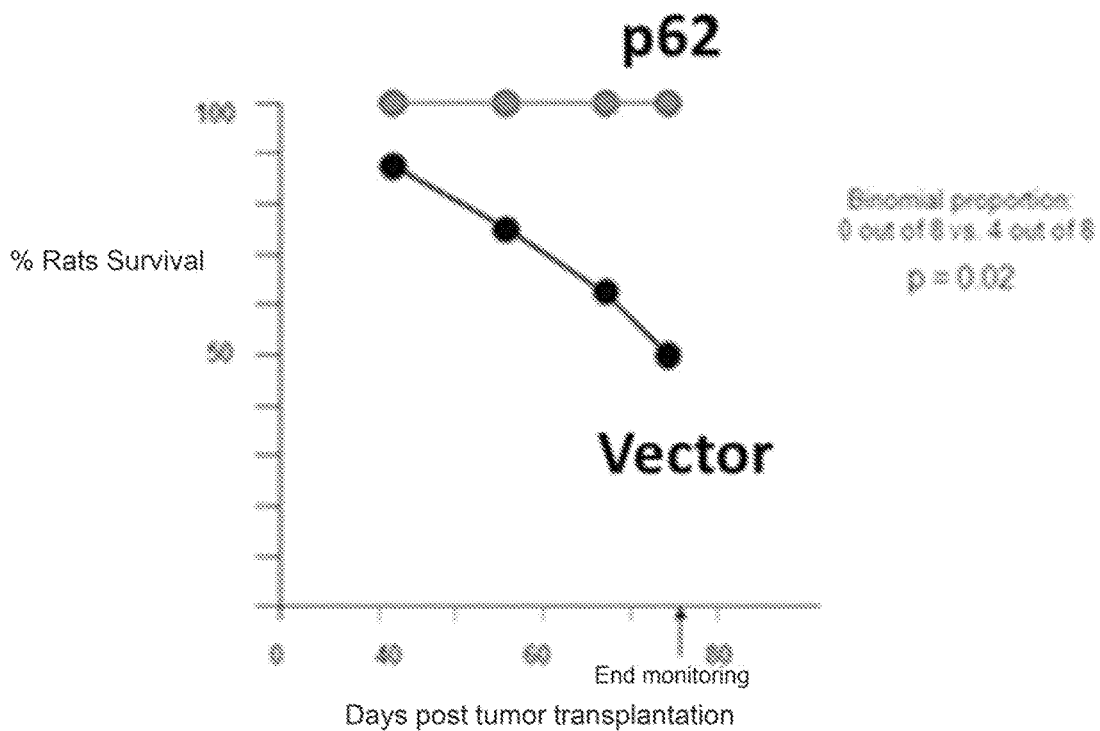
FIG. 10 shows a time course of rat survival in p62-vaccinated and control rats with T5 transplantable breast carcinoma.

Survival of tumor-implanted rats (8 vector- and 8 p62-immunized) was monitored over 75 days. 50% of the animal in the control group died while there were no animal deaths in p62-vaccinated group (FIG. 10).

Figure 11:
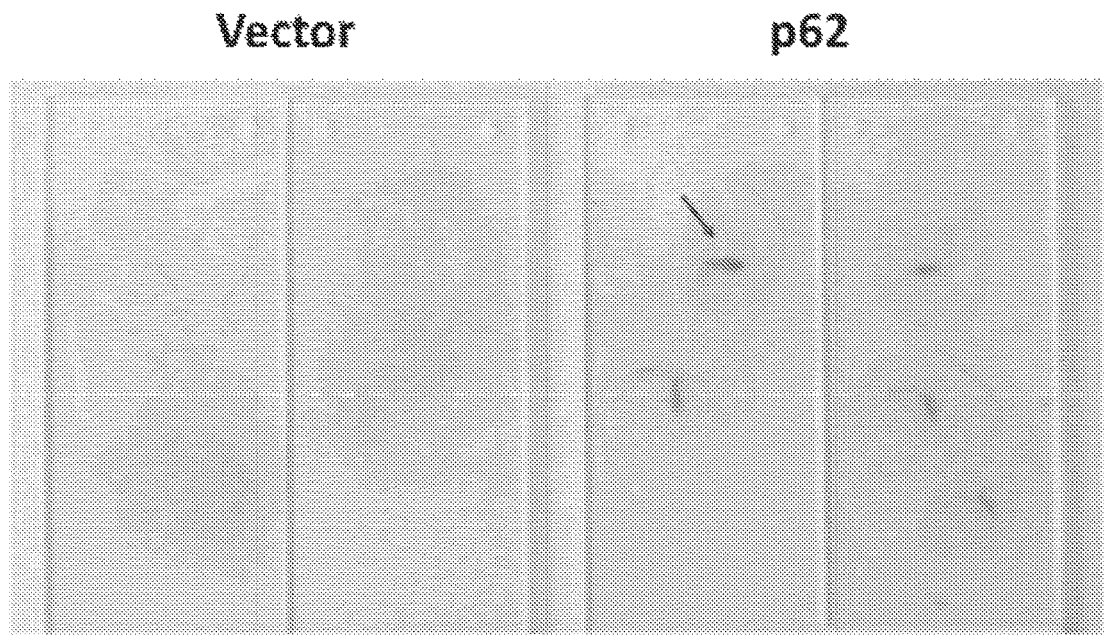
FIG. 11 shows tumor sections from p62- and control vector-vaccinated rats with T5 transplantable breast carcinoma.
Figure 12:
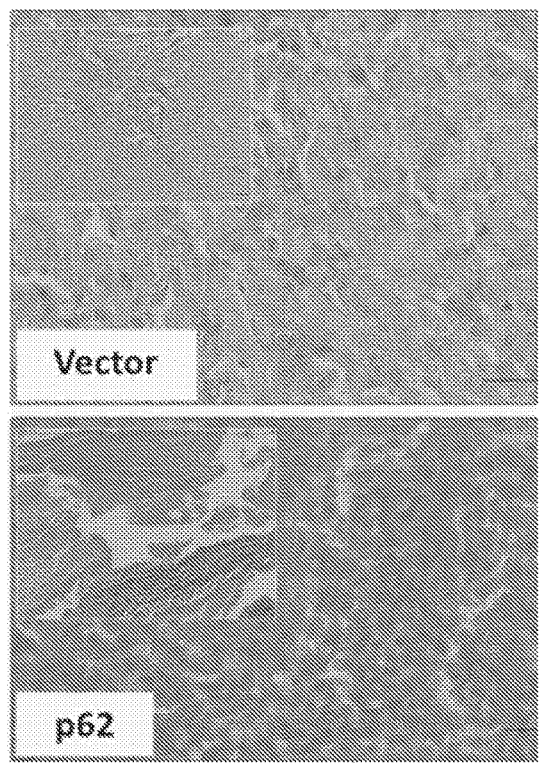
FIG. 12. shows Hematoxilin & Eosin (HE) staining of tumor sections from p62- and control vector-vaccinated rats with T5 transplantable breast carcinoma.

Histological analysis of the tumors revealed necrotic zones (FIG. 11). Intratumoral necrosis in rats receiving p62 DNA vaccine was similar to one observed in the tumors of mice receiving the p62 DNA vaccine (FIG. 12).

Consequently, the anti-tumor effect of p62 DNA vaccine was demonstrated in the second animal (rat) model, indicating that the p62 DNA vaccine can be used to treat breast cancer.

Example 5

Anti-metastatic Potency of p62 DNA Vaccine

Figure 13:
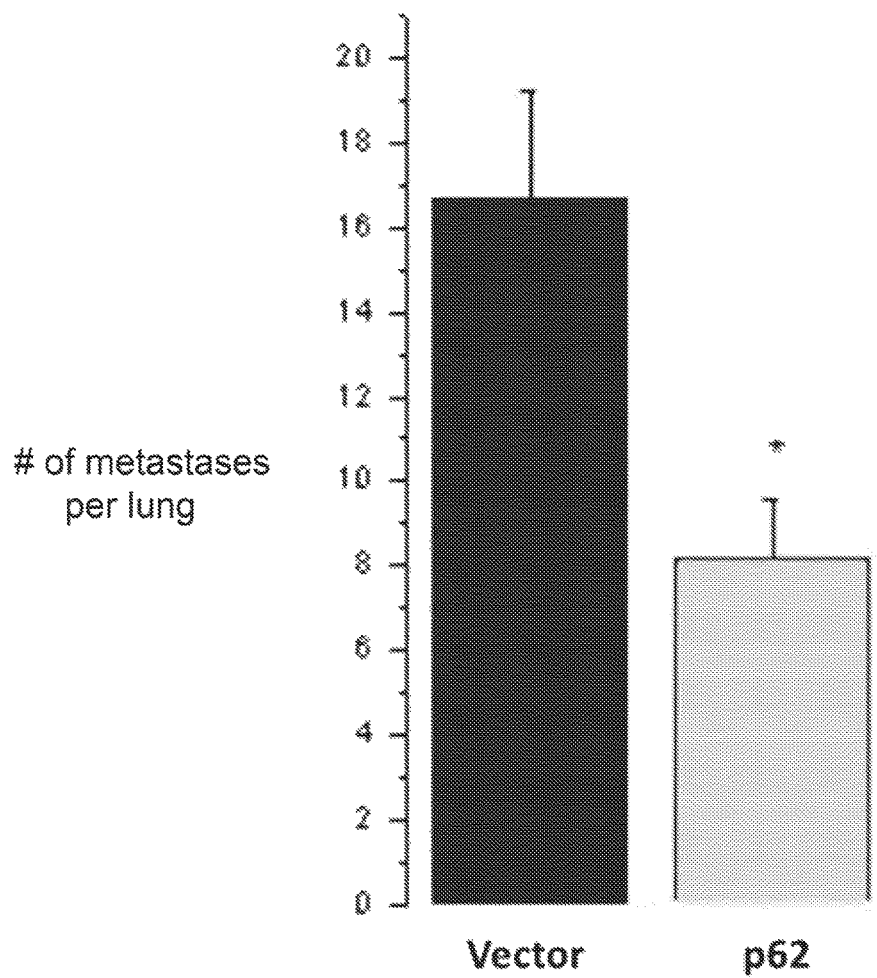
FIG. 13 shows a comparison of the number of Lewis Lung Carcinoma metastases between p62- and control vector-vaccinated mice.

Lewis lung carcinoma is a model officially accepted by Pharmacological Committee of Russian Federation, "Russian FDA", for testing drugs for anti-metastatic effects. 100 ug of plasmid was injected intramuscularly into each mice 4 weeks and 2 weeks prior to the challenge with tumor transplant, as well as 1, 8 and 15 days after the challenge. Fifteen animals per group were used. FIG. 13 shows that p62 vaccination reduced the number of metastases in lungs by 50% compared to control.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

The above disclosure is intended only to convey an understanding of the present invention to those skilled in the art, and is not intended to be limiting. It will be appreciated that various modifications to the disclosed embodiments are possible without departing from the scope of the invention. Therefore, the scope of the present invention should be construed solely by reference to the appended claims.

What is claimed is:

1. A composition comprising a cancer vaccine comprising a plasmid vector comprising a p62/SQSTM1 nucleic acid that encodes a polypeptide at least 98% identical to SEQ ID NO: 2 in a pharmaceutically acceptable carrier, wherein the cancer vaccine stimulates the immune defense mechanism in a host to restrict spreading or progression of tumors or metastatic lesions; and,
   a chemotherapeutic molecule selected from the group consisting of: cyclophosphamide, doxorubicin, paclitaxel, docetaxel, vinblastin, methotrexate, navelbine, capecitabine, mitomycin C, and 5-fluorouracil.

2. The composition of claim 1, wherein said p62/SQSTM1 encoding nucleic acid further comprises a nucleic acid encoding for a fusion polypeptide.

3. The cancer vaccine of claim 1, further comprising an adjuvant.

4. The cancer vaccine of claim 3, wherein said adjuvant is selected from the group consisting of: gel-type, microbial, particulate, oil-emulsion, surfactant-based, and synthetic adjuvant.

5. The cancer vaccine of claim 1, further comprising one or more co-stimulatory components.

6. The cancer vaccine of claim 5, wherein said one or more co-stimulatory components is selected from the group consisting of: a cell surface protein, a cytokine, a chemokine, and a signaling molecule.

7. The composition of claim 1, further comprising one or more molecules that block suppressive or negative regulatory immune mechanisms.

8. The cancer vaccine of claim 7, wherein said one or more molecules that block suppressive or negative regulatory immune mechanisms is selected from the group consisting of: anti-CTLA-4 antibody, anti-CD25 antibody, anti-CD4 antibody, and IL13Ra2-Fc.

9. The composition of claim 1, further comprising an anti-angiogenic molecule, an antibody, or a biological agent.

10. The composition of claim 1, wherein said cancer vaccine further comprises an optimized codon, a CpG stimulatory motif, a nucleic acid sequence for targeting of the endocytic or ubiquitin-processing pathways, a Marek's disease virus type 1 VP22 sequence, or a mucosal delivery vector.

11. A composition comprising:
    a cancer vaccine comprising a plasmid vector comprising a p62/SQSTM1 encoding nucleic acid encoding a polypeptide with a sequence according to SEQ ID NO.:2 in a pharmaceutically acceptable carrier, wherein the cancer vaccine stimulates the immune defense mechanism in a host to restrict spreading or progression of tumors or metastatic lesions; and, a chemotherapeutic molecule selected from the group consisting of: cyclophosphamide, doxorubicin, paclitaxel, docetaxel, vinblastin, methotrexate, navelbine, capecitabine, mitomycin C, and 5-fluorouracil.

12. The composition of claim 11, wherein said p62/SQSTM1 encoding nucleic acid further comprises a nucleic acid encoding for a fusion polypeptide.

13. The composition of claim 11, further comprising one or more molecules that block suppressive or negative regulatory immune mechanisms.

14. The composition of claim 11, wherein said cancer vaccine further comprises an optimized codon, a CpG stimulatory motif, a nucleic acid sequence for targeting of the endocytic or ubiquitin-processing pathways, a Marek's disease virus type 1 VP22 sequence, or a mucosal delivery vector.

* * * * *